US008188089B2

(12) United States Patent
Lee et al.

(10) Patent No.: US 8,188,089 B2
(45) Date of Patent: May 29, 2012

(54) TYLOPHORINE ANALOGS AS ANTITUMOR AGENTS

(75) Inventors: Kuo-Hsiung Lee, Chapel Hill, NC (US); Linyi Wei, Chapel Hill, NC (US); Kenneth F. Bastow, Chapel Hill, NC (US); Arnold Brossi, Bethesda, MD (US); Tian-Shung Wu, Tianan (TW)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 497 days.

(21) Appl. No.: 12/096,950

(22) PCT Filed: Dec. 20, 2006

(86) PCT No.: PCT/US2006/049035
§ 371 (c)(1),
(2), (4) Date: Jul. 28, 2008

(87) PCT Pub. No.: WO2007/081540
PCT Pub. Date: Jul. 19, 2007

(65) Prior Publication Data
US 2008/0300254 A1     Dec. 4, 2008

Related U.S. Application Data

(60) Provisional application No. 60/756,282, filed on Jan. 5, 2006.

(51) Int. Cl.
*A61K 31/496*   (2006.01)
*A61K 31/4525*  (2006.01)
*A61K 31/36*    (2006.01)
*C07D 317/70*   (2006.01)
*C07D 405/06*   (2006.01)

(52) U.S. Cl. .............. 514/254.11; 514/321; 514/467; 544/378; 546/197; 548/526; 549/342

(58) Field of Classification Search .......... None
See application file for complete search history.

(56) References Cited

U.S. PATENT DOCUMENTS
2005/0222418 A1    10/2005  Baker et al.

FOREIGN PATENT DOCUMENTS
WO    WO 01/23384 A1    4/2001

OTHER PUBLICATIONS

European Examination Report, EP 06 84 8033, May 25, 2009.
Supplemental European Search Report, EP 06 84 8033, Feb. 13, 2009.
Nacci V et al. Ricerche su sostanze ad attivita antiblastica. Farmaco, Societa Chimica Italiana, Pavia, IT. Jan. 1, 1972; 328(5): 399-410.
Database CAPLUS (online). Chemical Abstracts Service, Columbus, OH. Retrieved from STN accession No. 108:56407. Astract. 3 pages, (1988).
International Search Report and Written Opinion, PCT/US06/49035, date of mailing Sep. 12, 2007.
Damu Ag et al. Phenanthroindolizidine alkaloids from the stems of *Ficus septica*. J. Nat. Prod. 2005;68(7):1071-1075.
Stærk D et al. In vitro cytotoxic activity of phenanthroindolizidine alkaloids from *Cynanchum vincetoxicum* and *Tylophora tanakae* against drug-sensitive and multidrug-resistant cancer cells. J. Nat. Prod. 2002;65(9):1299-1302.
Thornhill SM et al. Natural treatment of perennial allergic rhinitis. Alternative Medicine Review. 2000;5(5):448-454.
Gao W et al. Novel mode of action of tylophorine analogs as antitumor compounds. Cancer Research. Jan. 15, 2004;64:678-688.

*Primary Examiner* — Emily Bernhardt
(74) *Attorney, Agent, or Firm* — Myers Bigel Sibley & Sajovec, P.A.

(57) ABSTRACT

Compounds of Formula I are described: preferably subject to the proviso that either (a) $R^2$ and $R^3$ together form —O—CH($R^{10}$)—O—, or (b) $R^5$ and $R^6$ together form —O—CH($R^{10}$)—O—, wherein $R^{10}$ is H, halo, or loweralkyl. Pharmaceutical salts, formulations, and methods of using the same in the treatment of cancer are also described.

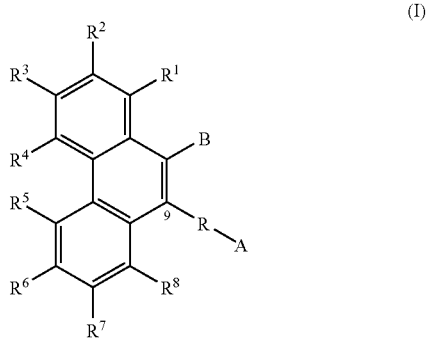

(I)

9 Claims, No Drawings

TYLOPHORINE ANALOGS AS ANTITUMOR AGENTS

RELATED APPLICATIONS

This application is a national phase application of PCT Application PCT/US2006/049035, filed Dec. 20, 2006, and published in English on Jul. 19, 2007, as International Publication No. WO 2007/081540, and which claims the benefit of United States Provisional patent application Ser. No. 60/756,282, filed Jan. 5, 2006, the disclosure of each of which is incorporated by reference herein in its entirety.

STATEMENT OF GOVERNMENT SUPPORT

This invention was made with government support under NIH grant CA 17625. The Government has certain rights to this invention.

FIELD OF THE INVENTION

The present invention concerns phenanthrine-based tylophorine analogs as active compounds, formulations thereof, and methods of use thereof, particularly in methods of treating cancer.

BACKGROUND OF THE INVENTION

Several plants of the *Tylophora* genus have been used medicinally as anti-inflammatory, antiarthritis, and anti-amoebic agents in East Asian countries (Jiangsu New Medical College. Dictionary of Chinese Traditional Medicine; Shanghai: Shanghai Science and Technology Publishing House, 1977; pp 1747; Baumgartner, B. et al., *Phytochemistry* 1990, 29, 33327-33330; Wu, P. L. et al., *Heterocycles* 2002, 57, 2401). In addition to various traditional therapeutic uses, tylophorine, the biologically active constituent, has been the target of synthetic modification for many years because of its profound cytotoxicity (Gellert, E.; Rudzats, R. *J. Med. Chem.* 1964; 7:361-362; Rao, K. V. et al., *J. Pharm. Sci* 1971; 60:1725-1726; Suffness, M.; Cordell, G. A. In The Alkaloids, Chemistry and Pharmacology, Brossi, A., Ed.; Academic Press: New York, 1985; Vol. 25, pp 3-355; Tanner, U.; Wiegrebe, W., *Arch. Pharm. (Weinheim)* 1993; 326:67-72). Tylophorine (1) (Chart 1) and its phenanthroindolizidine alkaloid analog (also referred to as *tylophora* alkaloids), have been isolated primarily from plants of the family Asclepiadaceae, including members of the genuses *Tylophora, Vincetoxicum, Pergularia, Cynanchum* (Gellert, E. In Alkaloids: Chemical and Biological Perspectives; Pelletier, S. W. Ed.; Academic Press: New York, 1987; pp 55-132; Gellert, E. The indolizidine alkaloids. *J. Nat. Prod.* 1982; 45:50-73; Govindachari, T. R. In The Alkaloids, Chemistry and Pharmacology, Manske, R. H. F. Ed.; Academic Press: New York, 1976; Vol. 9, 517-528; Bick, I. R. C.; Sinchai, W. In The Alkaloids, Chemistry and Pharmacology, Manske, R. H. F., Rodrigo, R. G. A, Eds.; Academic Press: New York, 1981; Vol 19, pp 193-220).

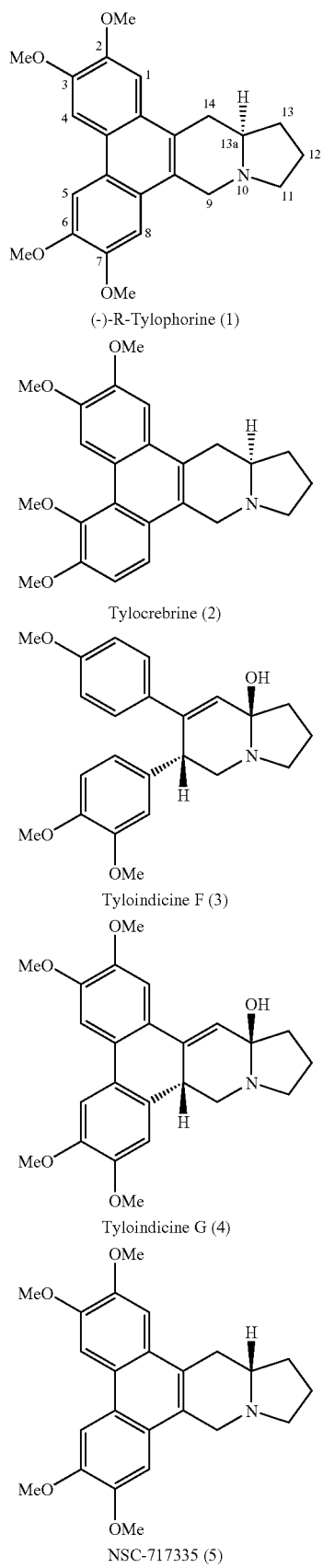

CHART 1

(-)-R-Tylophorine (1)

Tylocrebrine (2)

Tyloindicine F (3)

Tyloindicine G (4)

NSC-717335 (5)

The clinical use of chemotherapeutic agents against malignant tumors is successful in many cases, but suffers from major drawbacks. One drawback is lack of selectivity, which leads to severe systemic side effects and limited efficacy. Another major problem is the emergence/selection of drug-resistance.

The drug development failure of tylocrebrine (2) (Chart 1), a positional isomer of tylophorine, in 1966 was due to a central nervous system toxicity, manifested by ataxia and disorientation. This disappointing clinical result discouraged further consideration of these alkaloids for drug development. However, in the 1990s, tylophorine analogs deemed previously not to warrant further research were re-screened for antitumor potential by the National Cancer Institute (NCI) using a 60-tumor cell line panel. These compounds showed potent and uniform activity against 54 human tumor cell lines with mean $GI_{50}<10^{-10}$ M. Moreover, tylophorine F (3) and tylophorine G (4) were quite active toward refractory cancer cell lines including melanoma and lung cancer.

Recent studies (Gao, W. et al., *Cancer Res.* 2004; 64:678-688; Stærk, D. et al., *J. Nat. Prod.* 2002, 65, 1299-1302) have shown that tylophorine analogs exhibit potent cytotoxic activity against a broad range of human cancer cells and sublines resistant or cross-resistant to various conventional anticancer drugs, such as etoposide (VP-16), taxol, topotecan, adriamycin, cytosine arabinoside, gemcitabine, hydroxyurea, or camptothecin (CPT). Gao et al also found that NSC-717335 (5), a stereoisomer of tylophorine, significantly inhibits activator protein-1, CRE, and nuclear factor κB (NF-κB) mediated transcription. NF-κB has been suggested to be a mechanism of drug resistance because of its antiapoptotic role (Wang, C. Y. et al., *Nat. Med.* 1999, 5, 412-417). Other research implicates NF-κB in the regulation of p-glycoprotein, a well known mechanism of multidrug resistance to chemotherapy.

SUMMARY OF THE INVENTION

A first aspect of the present invention is a compound of Formula I:

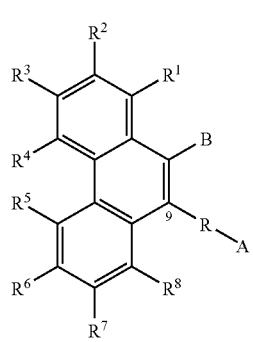

(I)

wherein:
R is C1-C4 alkylene;
A is substituted amine;
B is H, halo, loweralkyl, or loweralkenyl;
or A and B together form a fused ring or fused ring system containing at least one hetero atom selected from the group consisting of N, O, and S, which fused ring or fused ring system may be substituted or unsubstituted; and
$R^1$, $R^2$, $R^3$, $R^4$, $R^5$, $R^6$, $R^7$ and $R^8$ are each independently selected from the group consisting of H, halo, alkoxy, loweralkyl, and loweralkenyl;
or a pharmaceutically acceptable salt thereof.

In some embodiments, at least one of $R^2$, $R^3$, $R^4$, $R^5$, $R^6$ and $R^7$ is alkoxy.

In some embodiments, (a) $R^2$ and $R^3$ together form —O—CH($R^{10}$)—O—, or (b) $R^5$ and $R^6$ together form —O—CH($R^{10}$)—O—, wherein $R^{10}$ is H, halo, or loweralkyl;

A further aspect of the present invention is a pharmaceutical formulation comprising an active compound as described herein, in a pharmaceutically acceptable carrier (e.g., an aqueous carrier).

A still further aspect of the present invention is a method of treating a cancer, comprising administering to a human or animal subject in need thereof a treatment effective amount (e.g., an amount effective to treat, slow the progression of, etc.) of an active compound as described herein. Examples of cancers that may be treated include, but are not limited to, skin cancer, lung cancer including small cell lung cancer and non-small cell lung cancer, testicular cancer, lymphoma, leukemia, Kaposi's sarcoma, esophageal cancer, stomach cancer, colon cancer, breast cancer, endometrial cancer, ovarian cancer, central nervous system cancer, liver cancer and prostate cancer.

A still further aspect of the invention is the use of an active compound or active agent as described herein for the preparation of a medicament for carrying out a method of treatment as described herein.

DETAILED DESCRIPTION OF THE INVENTION

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety.

"Alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

"Alkenyl," as used herein, refers to a straight or branched chain hydrocarbon containing from 2 to 10 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

"Loweralkenyl" as used herein, is a subset of alkenyl and refers to a straight or branched chain hydrocarbon group containing from 1 to 4 carbon atoms.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

"Alkylthio" as used herein refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Cycloalkyl," as used herein, refers to a saturated cyclic hydrocarbon group containing from 3 or 4 to 6 or 8 carbons. Representative examples of cycloalkyl include, cyclopropyl, cyclobutyl, cyclopentyl, cyclohexyl, cycloheptyl, and cyclooctyl.

"Heterocycle," as used herein, refers to a monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like.

Heterocycle groups of this invention can be substituted with 1, 2, or 3 substituents, such as substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkoxycarbonyl, arylalkyl, aryloxy, carboxy, cyano, formyl, oxo, halo, haloalkyl, haloalkoxy, hydroxy, hydroxyalkyl, mercapto, nitro, sulfamyl, sulfo, sulfonate, —NR' R" (wherein, R' and R" are independently selected from hydrogen, alkyl, alkylcarbonyl, aryl, arylalkyl and formyl), and —C(O)NRR' (wherein, R and R' are independently selected from hydrogen, alkyl, aryl, and arylalkyl).

"Halo" as used herein refers to any halogen group, such as chloro, fluoro, bromo, or iodo.

"Oxo" as used herein, refers to a =O moiety.

"Oxy," as used herein, refers to a —O— moiety.

"Amine" or "amino group" is intended to mean the radical —NH$_2$.

"Substituted amino" or "substituted amine" refers to an amino group, wherein one or two of the hydrogens is replaced by a suitable substituent. Disubstituted amines may have substituents that are bridging, i.e., form a heterocyclic ring structure that includes the amine nitrogen as the linking atom to the parent compound. Examples of substituted amino include but are not limited to alkylamino, dialkylamino, and heterocyclo (where the heterocyclo is linked to the parent compound by a nitrogen atom in the heterocyclic ring or heterocyclic ring system).

"Alkylamino" is intended to mean the radical —NHR', where R' is alkyl.

"Dialkylamino" is intended to mean the radical NR'R", where R' R" are each independently an alkyl group.

"Treat" or "treating" as used herein refers to any type of treatment that imparts a benefit to a patient afflicted with a disease, including improvement in the condition of the patient (e.g., in one or more symptoms), delay in the progression of the disease, prevention or delay of the onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein means that a potential effect is partially or completely eliminated.

The present invention is concerned primarily with the treatment of human subjects, but may also be employed for the treatment of other animal subjects (i.e., mammals such as dogs, cats, horses, etc. or avians) for veterinary purposes. Mammals are preferred, with humans being particularly preferred.

A. Active Compounds.

Active compounds of the present invention are, in general, compounds of Formula I:

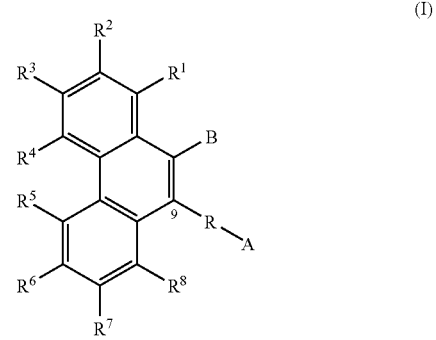

(I)

wherein:

R is C1-C4 alkylene (e.g., —CH$_2$—, —CH$_2$CH$_2$—, —CH$_2$CH$_2$CH$_2$—));

A is substituted amine;

B is H, halo, loweralkyl, or loweralkenyl;

or A and B together form a fused ring or fused ring system containing at least one hetero atom selected from the group consisting of N, O, and S, which fused ring or fused ring system may be substituted or unsubstituted; and $R^1$, $R^2$, $R^3$, $R^4$, $R^5$, $R^6$, $R^7$ and $R^8$ are each independently selected from the group consisting of H, halo, alkoxy, loweralkyl, and loweralkenyl;

subject to the proviso that at least one of $R^2$, $R^3$, $R^4$, $R^5$, $R^6$ and $R^7$ is alkoxy;

and subject to the proviso that either (a) $R^2$ and $R^3$ together form —O—CH($R^{10}$)—O— (as shown in Formula Ia below), or (b) $R^5$ and $R^6$ together form —O—CH($R^{10}$)—O— (as shown in Formula Ib below), wherein $R^{10}$ is H, halo, or loweralkyl;

and pharmaceutically acceptable salts thereof.

More particular examples of compounds of Formula I include compounds of Formulas Ia and Ib:

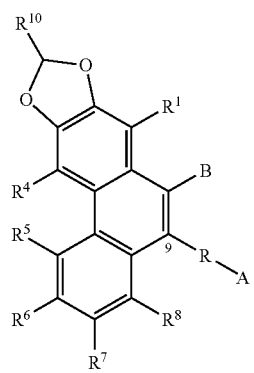

(Ia)

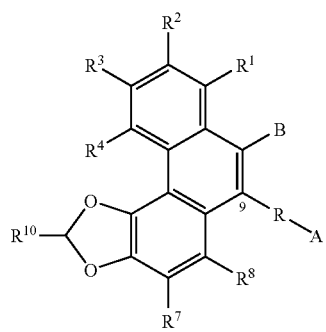

(Ib)

wherein A, B, R, $R^1$, $R^2$, $R^3$, $R^4$, $R^5$, $R^6$, $R^7$, $R^8$ and $R^{10}$ are as given above.

More particular examples of substituted amine substituents "A" include, but are not limited to substituents of the general formula —$NR^{11}R^{12}$, where $R^{11}$ is H, alkyl, hydroxy, hydroxyalkyl, alkoxy, alkoxyalkyl, amino, or aminoalkyl, and $R^{12}$ is alkyl, hydroxy, hydroxyalkyl, alkoxy, alkoxyalkyl, amino, aminoalkyl, alkylaminoalkyl, alkylthio, or alkylthioalkyl, each of which may be substituted or unsubstitued.

More particular examples of substituted amine substituents "A", where "A" is a heterocyclic group, include but are not limited to:

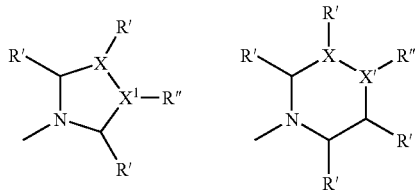

wherein X and X' are each independently selected from N, O, and C, and each R' and R" is independently selected from the group consisting of H, alkyl, hydroxyalkyl, alkenyl, alkoxy, halo, oxo (=O), =S, amino, substituted amino, alkoxyalkyl, alkylthiolkyl, and aryl (e.g., phenyl), all of which are optionally substituted (e.g., with hydroxyl, preferably at the para position) subject to the proviso that the corresponding R' is absent when X is O or S.

In some embodiments, each R' is H.

In some embodiments, R" is hydroxyalkyl or p-hydroxyaryl.

Specific examples of substituted amine substituents "A" include, but are not limited to:

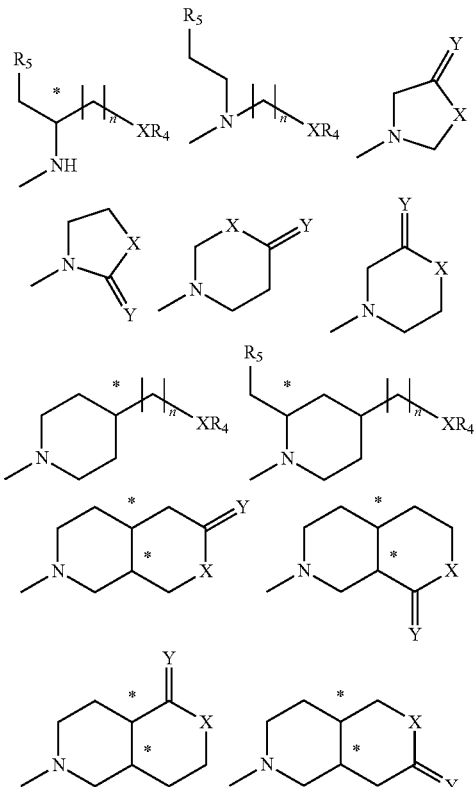

X = N, O; Y = O, S;
n = 1-7;
$R_4$ = H, Alkyl, Substituted alkyl;
$R_5$ = H, Hydroxy, Alkyloxy, Amino group, Aminoalkyls;
*: Chiral Center, R, S, or RS mix Examples of fused rings and fused ring systems which A and B may together form include, but are not limited to, the following:

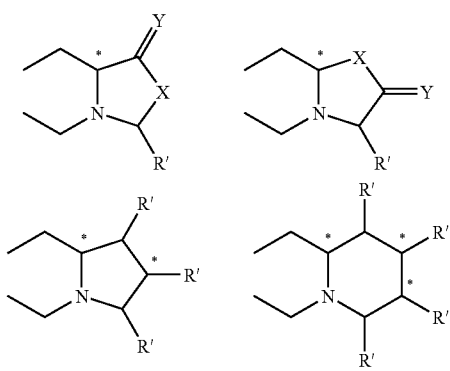

wherein X is N or O; Y is O or S, and each R' is independently selected from the group consisting of H, alkyl, alkenyl, alkoxy, halo, oxo, amino, substituted amino, alkoxyalkyl, and alkylthiolkyl.

Specific examples of fused rings or fused ring systems which "A" and "B" may together form include, but are not limited to:

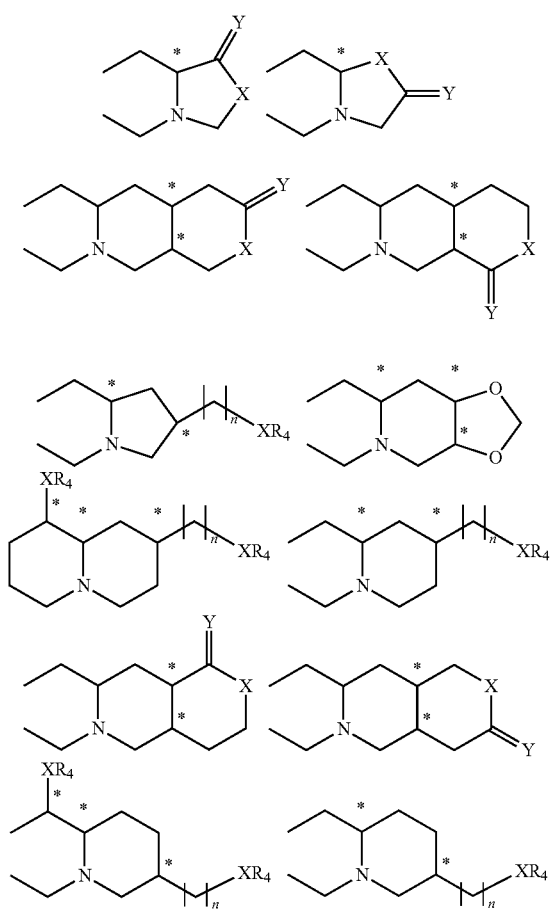

X = N, O; Y = O, S;
n = 1-7;
R$_4$ = H, Alkyl, Substituted alkyl;
R$_5$ = H, Hydroxy, Alkyloxy, Amino group, Aminoalkyls;
*: Chiral Center, R, S, or RS mix In some embodiments, A is:

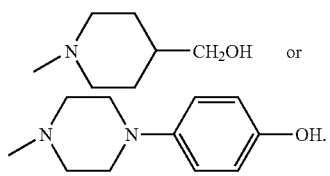

In some embodiments of the foregoing, $R^2$ and $R^3$ are both alkoxy, such as methoxy or ethoxy.

In some embodiments of the foregoing, $R^3$ is alkoxy, such as methoxy or ethoxy.

In some embodiments of the foregoing, $R^6$ is alkoxy, such as methoxy or ethoxy.

In some embodiments of the foregoing, $R^5$ and $R^6$ are both alkoxy, such as methoxy or ethoxy.

In some embodiments of the foregoing, $R^6$ and $R^7$ are both alkoxy, such as methoxy or ethoxy.

Compounds of the present invention can be made in accordance with known techniques, such as the Perkin reaction (See, Wassmundt, F. W.; Kiesman, W. F., *J. Org. Chem.* 1995; 60:196-201; Lebrun, S et al., *Tetrahedron* 1999, 55, 2659-2670) and improved free-radical Pschorr cyclization (Gellert, E. In Alkaloids: Chemical and Biological Perspectives; Pelletier, S. W. Ed.; Academic Press: New York, 1987; pp 55-132.), or variations thereof which will be apparent to those skilled in the art based upon the disclosure provided herein.

B. Formulations and Pharmaceutically Acceptable Salts.

The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

The compounds of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3:318 (1986)) and typically take the form of an optionally buffered aqueous solution of the active compound. Suitable formulations comprise citrate or bis/tris buffer (pH 6) or ethanol/water and contain from 0.01 to 0.2M active ingredient.

C. Methods of Use.

In addition to the compounds of the formulas described herein, the present invention also provides useful therapeutic methods. For example, the present invention provides a method of inducing cytotoxicity against tumor cells, or treating a cancer or tumor in a subject in need thereof.

Cancer cells which may be inhibited include cells from skin cancer, small cell lung cancer, non-small cell lung cancer, testicular cancer, lymphoma, leukemia, Kaposi's sarcoma, esophageal cancer, stomach cancer, colon cancer, breast cancer, endometrial cancer, ovarian cancer, central nervous system cancer, liver cancer and prostate cancer.

Subjects which may be treated using the methods of the present invention are typically human subjects although the methods of the present invention may be useful for veterinary purposes with other subjects, particularly mammalian subjects including, but not limited to, horses, cows, dogs, rabbits, fowl, sheep, and the like. As noted above, the present invention provides pharmaceutical formulations comprising the compounds of formulae described herein, or pharmaceutically acceptable salts thereof, in pharmaceutically acceptable carriers for any suitable route of administration, including but not limited to oral, rectal, topical, buccal, parenteral, intramuscular, intradermal, intravenous, and transdermal administration.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The present invention is explained in greater detail in the following non-limiting examples.

EXAMPLE 1

Phenanthrene-Based Tylophorine Derivatives (PBTs)

This example describes our initial design and synthesis of novel polar water-soluble PBTs, cytotoxicity evaluation against the human A549 lung cancer cell line, and structure-activity relationships (SAR) of this new compound class. The goal of this study is to generate and optimize phenanthrene derivatives as promising clinical trial candidates for treating cancer.

Chemistry. Compounds 10-49 were synthesized following the efficient reported procedure (Wassmundt, F. W.; Kiesman, W. F.; Soluble catalysts for improved Pschorr cyclizations. *J. Org. Chem.* 1995, 60, 196-201.) outlined in Scheme 1. A commercially available substituted O-nitrobenzaldehyde (3a, b) was treated with 4-methoxy or -benzyloxyphenyl acetic acid (4a,b) in the presence of $Ac_2O$ (Perkin condensation) to yield an intermediate nitro-substituted cinnamic acid (5a-c). The nitro group of 5 was converted to an amine using ammoniacal ferrous sulfate ($FeSO_4$) to provide the amino-substituted cinnamic acid (6a-c). Phenanthrenes 7a-c, which are the key intermediates in our method, were formed by an improved free-radical Pschorr cyclization in high yield. Compound 6 was treated with sodium nitrite in 48% fluoroboric acid, and the resulting diazonium tetrafluoroborate was then efficiently cyclized to the phenanthrene-9-carboxylic acid (7) using catalytic ferrocene. Intermediates 7a-c were then condensed with the appropriate -hydroxybenzotriazole (HOBT) to give the amido-substituted phenanthrene (8). These mild conditions avoid the production of degradation products resulting from the acidic instability of the methylenedioxy group. Selective reduction of the amide carbonyl group to a methylene was achieved by using borane-methyl sulfide complex (BMS, 2.0M solution in THF) to provide 9. The C-9 side chain methyl ester was converted to carboxylic acid and hydroxymethyl groups by basic hydrolysis and lithium aluminum hydride reduction, respectively. The 6-phenolic analogs were prepared by hydrogenolysis ($H_2$, Pd/C) of the benzyloxy protecting group.

Results and discussion. Tables 1-3 summarize the structures of newly synthesized PBTs (7a-c, 10-42) and their cytotoxic activity ($EC_{50}$) against the A549 lung cancer cell line. Etoposide (VP-16) was used as the reference compound.

Scheme 1

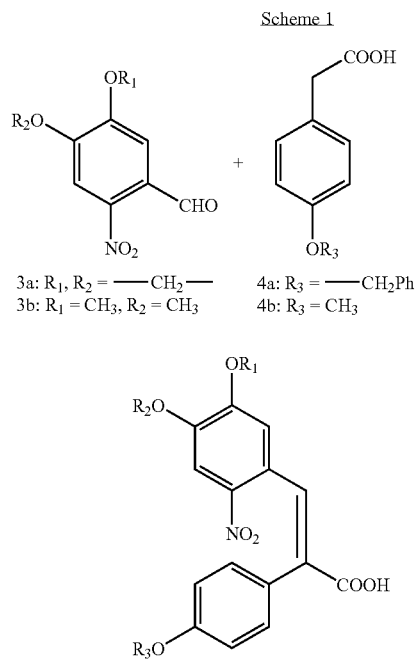

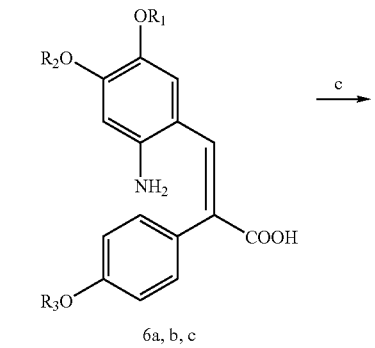

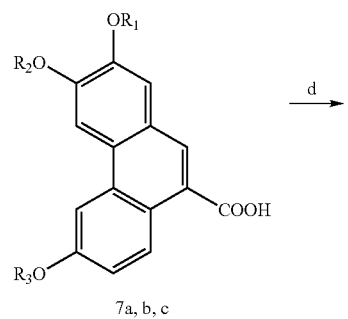

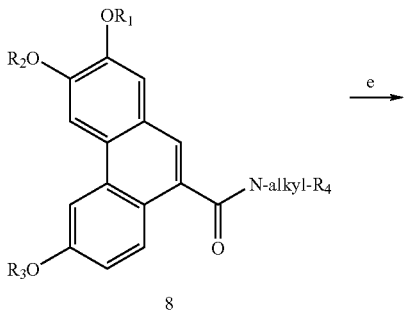

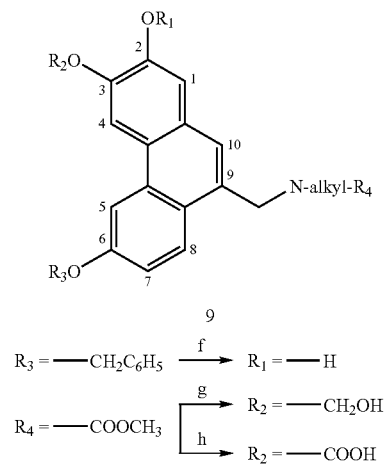

Reagents and conditions: a: $Ac_2O/Et_3N$ b: $FeSO_4/NH_4OH$ c: $NaNO_2$/Fluoboric acid; Ferrocene/acetone d; EDC, DMAP, HOBt/DMF e: BMS/THF f: $H_2$, Pd/C/MeOH g: $LiAlH_4$/THF h: NaOH/MeOH (1:1)

TABLE 1

SAR of 2,3-Methylenedioxy-6-alkyloxy-9-substituted PBT Analogs

| Compound | R₁ | R₂ | IC$_{50}$ (μM)$^{a,b}$ |
|---|---|---|---|
| 7a | —CH₂C₆H₅ | —COOH | NA |
| 7b | —CH₃ | —COOH | NA |
| 10 | —CH₂C₆H₅ | —CONH(CH₂)₅COOMe | 41.2 |
| 11 | —CH₂C₆H₅ | —CONH(CH₂)₅COOH | 41.2 |
| 12 | —CH₂C₆H₅ | —CH₂NH(CH₂)₅COOH | 1.6 |
| 13 | —CH₂C₆H₅ | —CH₂NH(CH₂)₅CH₂OH | 1.1 |
| 14 | —CH₂C₆H₅ | —CH₂NH(CH₂)₄COOMe | 17.0 |
| 15 | —CH₂C₆H₅ | —CH₂NH(CH₂)₄COOH | 2.2 |
| 16 | —CH₂C₆H₅ | N-acetyl proline (HOOC) | 42.6 |
| 17 | —CH₂C₆H₅ | N-ethyl proline methyl ester (MeOOC) | 32.1 |
| 18 | —CH₂C₆H₅ | N-ethyl proline (HOOC) | 4.4 |
| 19 | —CH₂C₆H₅ | N-ethyl prolinol (HO—) | 1.8 |
| 20 | —CH₂C₆H₅ | N-ethyl pipecolic acid (HOOC) | 3.2 |
| 21 | —CH₂C₆H₅ | N-ethyl pipecolinol (HO—) | 1.3 |
| 22 | —H | N-acetyl proline (HOOC) | 39.7 |
| 23 | —H | N-ethyl proline (HOOC) | 41.2 |
| 24 | —H | N-ethyl pipecolic acid (HOOC) | 39.7 |
| 25 | CH₃ | —CONH(CH₂)₄COOH | 73.3 |
| 26 | CH₃ | —CH₂NH(CH₂)₄COOMe | 25.3 |
| 27 | CH₃ | —CH₂NH(CH₂)₄COOH | 1.3 |
| 28 | CH₃ | —CH₂NH(CH₂)₄CH₂OH | 0.27 |
| 29 | CH₃ | N-acetyl proline (HOOC) | 5.3 |
| 30 | CH₃ | N-ethyl proline methyl ester (MeOOC) | 73.8 |
| 31 | CH₃ | N-ethyl proline (HOOC) | 2.1 |
| 32 | CH₃ | N-ethyl prolinol (HO—) | 0.7 |
| 33 | CH₃ | N-ethyl pipecolic acid (HOOC) | 0.5 |

TABLE 1-continued

SAR of 2,3-Methylenedioxy-6-alkyloxy-9-substituted PBT Analogs

| Compound | R₁ | R₂ | IC₅₀ (μM)$^{a,b}$ |
|---|---|---|---|
| 34 | CH₃ | HO-CH₂-(N-ethylpiperidin-2-yl) | 0.16 |

$^a$Etoposide (VP-16) used as positive control, EC₅₀ = 1.4 μM.
$^b$NA = Not Active

TABLE 2

SAR of 2,3,6-Trimethyoxy-9-substituted PBT Analogs.

| Compound | R | IC₅₀ (μM) |
|---|---|---|
| 7c | —COOH | NA |
| 35 | —CH₂NH(CH₂)₅COOH | 9.7 |
| 36 | —CH₂NH(CH₂)₅CH₂OH | 2.7 |
| 37 | HOOC-(N-ethylpiperidin-2-yl) | 9.7 |
| 38 | HO-CH₂-(N-ethylpiperidin-2-yl) | 6.3 |

$^a$Etoposide (VP-16) used as positive control, EC₅₀ = 1.4 μM.
$^b$NA = Not Active

TABLE 3

SAR of seco-PBT Analogs

| Compound | Structure | IC₅₀ (μM) |
|---|---|---|
| 39 | (proline-COOH with carbonyl-linked stilbene, MeO/MeO/NO₂/OMe substituents) | 80 |
| 40 | (proline-COOH with CH₂-linked stilbene) | 45.2 |
| 41 | (prolinol HO-CH₂ with CH₂-linked stilbene, NO₂) | 11.7 |
| 42 | (prolinol HO-CH₂ with CH₂-linked stilbene, no NO₂) | 52.2 |

Etoposide (VP-16) used as positive control, EC₅₀ = 1.4 μM

Structure-Activity Relationship (SAR) Analysis. All three intermediate phenanthrene-9-carboxylic acids 7a-c were inactive. Thus, the rigid, planar phenanthrene system is not sufficient for cytotoxic activity, and an appropriate C-9 side chain is a factor. However, the phenanthrene system is required for cytotoxic activity, as the seco analogues 39-42, which contain an active proline side chain (see discussion below) but only a stilbene skeleton, were also inactive.

Active analogs contained both cyclic (pyrrole/proline, piperidine/pipecolinic acid) and acyclic (aminopentanoic, aminohexanoic acids) nitrogen-containing side chains at the C-9 position of phenanthrene. However, the linkage between the nitrogen and the phenanthrene was significant. Reduction of the amide carbonyl to methylene could dramatically increase the cytotoxic activity as shown in the comparison of 16 (L-proline amide, carbonyl linkage, $EC_{50}$ 42.6 µM) and 18 (methylene linkage, $EC_{50}$ 4.4 µM). This observation (carbonyl, unfavorable or less favorable; methylene, favorable) also could be seen in comparison of 11/12, 22/23, and 25/27. A simple explanation for this observation could possibly be the difference in configurational constraint. The carbonyl is conjugated with the phenanthrene ring and, thus, extends the coplanarity, while the methylene substituent can rotate freely around the C—C bond. The former geometric restriction appears to disfavor cytotoxic activity and may prevent the molecule from attaining the optimal conformation for binding to an assumed biological target.

On the phenanthrene skeleton, changing the benzyloxy moiety at the C-6 position to a hydroxy group was detrimental to activity (cf. 18/23 and 20/24). In addition, active compounds with a 6-benzyloxy moiety (15 and 18-21, $EC_{50}$ 1.3-4.4 µM) were generally slightly less potent than corresponding analogs with a 6-methoxy group (27 and 31-34, $EC_{50}$ 0.16-2.1 µM). Thus, the rank order of potency at the phenanthrene C-6 position was methoxy>benzyloxy >>hydroxyl, suggesting that this position cannot tolerate the introduction of a polar moiety. A hydrophilic moiety may be disfavored because a hydrophobic interaction occurs at this position between the compound and biological target that is involved in cytotoxic activity.

Interestingly, active compounds with a 2,3-methylenedioxy group (33 and 34, $EC_{50}$ 0.5 and 0.16 µM) were up to 40 times more potent than the corresponding compounds with a 2,3-dimethoxy moiety (37 and 38, $EC_{50}$ 9.7 and 6.3 µM). Thus, the five-membered methylenedioxy ring extension at the phenanthrene C2-C3 is quite favorable for cytotoxic activity.

In the amino side chain, when the terminal carboxylic acid group was masked as the methyl ester, the cytotoxic activity was diminished drastically or abolished (e.g., 14/15, 17/18, 26/27, 30/31). However, reduction of the carboxylic acid to the hydroxymethyl generally increased activity, both in cyclic (18/19, 20/21, 31/32, 33/34, 37/38) and acyclic (12/13, 27/28, 35/36) analogs. Thus, the rank order of potency of the terminal polar substituent was hydroxy>carboxylic acid>>methyl ester.

In summary, the favorable modification for these novel PBTs are as follows. 1) A planar phenanthrene system is important, but not sufficient for cytotoxic activity. 2) A N-hydrophilic substituent at the C-9 position is desirable for the enhanced cytotoxicity and should be linked through a methylene rather than a carbonyl group. 3) This C-9 N-hydrophilic substituent is ideal for the introduction of a polar moiety. Analogs containing terminal carboxylic acid or hydroxymethyl groups are more favorable than those with methyl esters. 4) On the phenanthrene skeleton, a methoxy substituent best fits both the steric and electronic requirements at the C-6 position and is preferred over benzyloxy and hydroxy groups. 5) Adding a methylenedioxy ring at the 2,3 position of the planar phenanthrene system can enhance the cytotoxic activity and led to the most potent derivatives.

Experimental Section. Melting points were measured using a Fisher Johns melting apparatus without correction. Proton nuclear magnetic resonance ($^1$H NMR) spectra were measured on a 300 MHz Varian Gemini 2000 spectrometer using TMS as internal standard. The solvent used was $CDCl_3$ unless indicated. Mass spectra were recorded on a PE-Sciex API-3000 LC/MS/MS instrument equipped with a Turbo IonsSpray ion source. Elemental analyses were performed by Atlantic Microlab, Inc., Norcross, Ga. All target compounds were analyzed for C, H, N and gave values within +/−4% of the theoretical values. Thin-layer chromatography (TLC) was performed on PLC silica gel 60 $F_{254}$ plates (0.5 mm, Merck). Biotage Flash+ and Isco Companion systems were used as medium-pressure column chromatography. Silica gel (200-400 mesh) from Aldrich, Inc., was used for column chromatography. 4-Benzyloxyphenylacetic acid and 3,4-methylenedioxy-6-nitrobenzaldehyde were purchased from TCI. L-Pipecolinic acid and isonipecotic acid were commercially available from Lancaster. All other chemicals were obtained from Aldrich, Inc. and Fisher, Inc.

General preparation. Phenanthrene-9-carboxylic acids 7a and 7b were synthesized following a reported procedure (Rubinstein, L. V.; Shoemaker, R. H.; Paull, K. D.; Simon, R. M.; Tosini, S.; Skehan, P.; Scudiero, D. A.; Monks, M. R. Comparison of in vitro anticancer-drug-screening data generated with a tetrazolium assay versus a protein assay against a diverse panel of human tumor cell lines. *J. Natl. Cancer Inst.* 1990, 82, 1113-1118.)

A solution of 3,4-methylenedioxy-6-nitrobenzaldehyde (12 mmol), triethyl amine (12 mmol), and 4-benzyloxy- or 4-methoxy-phenylacetic acid (17 mmol) was refluxed with stirring under Ar for 40 min. Water (30 ml) was added to the reaction mixture and the temperature was maintained between 90° C. and 100° C. during the addition. The reaction mixture was cooled to rt and the solid was collected by filtration and recrystallized from EtOH.

To a solution of the nitrocinnamic acid (7 mmol) in 10% aqueous $NH_4OH$ (100 ml) was added ferrous sulfate heptahydrate (15 g) dissolved in distilled water (100 mL) and concentrated aqueous $NH_4OH$ (100 mL). The reaction mixture was refluxed for 1.5 h, cooled to 40° C., filtered through Celite, and acidified with HOAc (100 mL). The resulting solid was collected by filtration and recrystallized from EtOH to yield the aminocinnamic acid.

A solution composed of the aminocinnamic acid (3 mmol), NaOH (33 mmol) and $NaNO_2$ in water (10 mL) was added dropwise over 30 min with stirring to 48% fluoroboric acid (43 mmol) at 0-5° C. The mixture was stirred for 1 h, after which sulfamic acid was added until the mixture tested negative to starch-iodide paper. The crude solid was collected by filtration, dissolved in anhydrous acetone (10 mL) and then added dropwise with stirring over a 15 min period to ferrocene (0.056 g, 0.3 mmol) in acetone at rt. After an additional 15 min of stirring, the green reaction mixture was added to water (100 mL). A light-yellow precipitate was collected and the trace amount of ferrocene was removed in vacuo to afford the phenanthrene-9-carboxylic acid.

General Procedure for the protection of cycloalkylamino acid (a): To a solution of cycloalkylamino acid (4 mmol) in dry MeOH (4 mL) was added dropwise $SOCl_2$ (0.4 mL) at −30° C. The reaction mixture was warmed to rt and refluxed for 1 h. Then the solvent was removed in vacuo and the product was used in the next reaction without further purification.

General Procedure for the Protection of Acyclic Alkylamino Acid (b)

To a solution of dry MeOH (3 mL) was added dropwise acetyl chloride (0.45 mL) at 0° C. After 10 min stirring, the amino acid was added to the solution in portions. The mixture was warmed to rt and refluxed for 2 h, then the solvent was removed in vacuo and the product was used in the next reaction without further purification.

General Procedure for the peptide bond condensation reaction (c): To a solution of phenanthrene-9-carboxylic acid (4 mmol), 4-(dimethylamino)pyridine (DMAP) (2 mmol), 1-hydroxybenzotriazole (HOBT) (4 mmol) in 20 mL DMF was added NMM (1.028 mL). After the mixture was stirred at 0° C. for 15 min, N-(3-dimethylaminopropyl)-N'-ethylcarbodiimide hydrochloride (EDC) (4.4 mmol) was added in portions, then methyl protected amino acid (4.4 mmol) was added after 30 min stirring. The reaction mixture was stirred overnight at rt and partitioned between EtOAc and water. The organic layer was washed with brine, saturated NaHCO$_3$ and 1N HCl, dried over Na$_2$SO$_4$, and concentrated in vacuo. The crude product was chromatographed using Biotage Flash+ and Isco Companion systems using a 40 g silica cartridge and EtOAc/hexane as eluant.

General Procedure for the carbonyl reduction reaction (d): To a stirred solution of 9-amido-substituted phenanthrene (8 in FIG. 1, 2 mmol) in THF (20 mL) was added dropwise borane-methyl sulfide (BMS) (4 mL, 2.0M solution in THF). The reaction mixture was stirred at rt overnight and quenched with 1N HCL. THF was removed in vacuo, and the residue was partitioned between CH$_2$Cl$_2$ and water. The organic layer was dried, filtered, and evaporated to afford the target product (9 in FIG. 1). The crude product was chromatographed using Biotage Flash+ and Isco Companion systems using MeOH/CH$_2$Cl$_2$ as eluant.

General Procedure for the basic hydrolysis reaction (e): A solution of ester in a 1:1 mixture of 4N NaOH and MeOH was refluxed for 4 h. The reaction mixture was acidified and partitioned between 10% MeOH/CH$_2$Cl$_2$ and 1N HCl. The organic layer was dried over Na$_2$SO$_4$, filtered, and evaporated. The crude product was chromatographed using Biotage Flash+ and Isco Companion systems using MeOH/CH$_2$Cl$_2$ as eluant.

General Procedure for the LiAlH$_4$ reduction (f): to a suspension of methyl ester (1 mmol) in 15 ml dry THF was added LiAlH$_4$ (1 g) in portions at 0° C. After addition, the reaction mixture was refluxed for 4 h, and then cooled to 0° C. The reaction mixture was quenched with methnol, and then 10% Rochelle salt was added. The reaction mixture was extracted with water and 10% MeOH/CH$_2$Cl$_2$. The organic layer was dried over Na$_2$SO$_4$, and the crude product was chromatographed using Biotage Flash+ and Isco Companion systems using MeOH/CH$_2$Cl$_2$ as eluant.

General Procedure for the catalytic cleavage (g): A solution of benzyoxy derivative (1 mmol) and Pd/C (10%) was hydrogenated in a Parr apparatus (30 psi) for 2 h. The reaction mixture was filtrated through Celite, and filtrate was concentrated in vacuo and was chromatographed using Biotage Flash+ and Isco Companion systems using MeOH/CH$_2$Cl$_2$ as eluant.

2,3-Methylenedioxy-6-benzyloxy-phenanthrene-9-carboxylic acid (7a). 75% yield over two steps; mp 263-265° C.; $^1$H NMR (400.13 MHz) δ 8.40 (d, J=4 Hz, 1H), 7.92 (d, J=2 Hz, 1H), 7.88 (s, 1H), 7.52 (m, 2H), 7.38 (m, 5H), 7.26 (dd, J=4 Hz, 2 Hz, 1H), 6.14 (d, J=4 Hz, 2H), 5.35 (d, J=7 Hz, 2H); MS (DCI/NH$_3$) m/e: 373 (M+H)$^+$.

2,3-Methylenedioxy-6-methoxy-phenanthrene-9-carboxylic acid (7b). 78% yield; white powder; mp 293-295° C.; $^1$H NMR (400.13 MHz) δ 7.67 (s, 1H), 7.60 (d, J=4 Hz, 1H), 7.22 (dd, J=4 Hz, 2 Hz, 1H), 6.92 (s, 1H), 6.89 (d, J=2 Hz, 1H), 6.70 (s, 1H), 5.98 (s, 2H), 3.79 (s, 3H); MS (DCI/NH$_3$) m/e: 297 (M+H)$^+$.

2,3,6-Trimethoxyphenanthrene-9-carboxylic acid (7c). 79% yield; white powder; mp 241-243° C.; $^1$H NMR (400.13 MHz) δ 8.93 (d, J=4 Hz, 1H), 8.33 (s, 1H), 7.84 (d, J=2 Hz, 1H), 7.82 (s, 1H), 7.23 (s, 1H), 7.22 (dd, J=4 Hz, 2 Hz, 1H), 4.07 (s, 3H), 3.98 (s, 3H), 3.97 (s, 3H), MS (DCI/NH$_3$) m/e: 314 (M+H)$^+$.

Methyl N-(2,3-methylenedioxy-6-benzyloxy-phenanthr-9-ylcarbonyl)-6-aminohexanoate (10). General procedure c from 7a (92%); colorless syrup; $^1$H NMR (400.13 MHz) δ 8.09 (d, J=4 Hz, 1H), 7.81 (d, J=2 Hz, 1H), 7.82 (s, 1H), 7.74 (d, J=4 Hz, 2H), 7.45 (s, 1H), 7.33 (t, J=4 Hz, 2H), 7.26 (m, 1H), 7.20 (dd, J=4 Hz, 2 Hz, 1H), 7.09 (s, 1H), 6.03 (s, 2H), 5.18 (s, 2H), 3.41 (s, 3H), 3.28 (m, 2H), 2.28 (t, J=6 Hz, 2H), 1.61 (m, 2H), 1.56 (m, 2H), 1.38 (m, 2H); MS (DCI/NH$_3$) m/e: 500 (M+H)$^+$.

N-(2,3-methylenedioxy-6-benzyloxy-phenanthr-9-ylcarbonyl)-6-aminohexanoic acid (11). General procedure e from 10 (100%); white needles; mp 198-200° C.; $^1$H NMR (400.13 MHz) δ 8.06 (d, J=4 Hz, 1H), 7.79 (d, J=2 Hz, 1H), 7.75 (s, 1H), 7.48 (s, 1H), 7.40 (d, J=4 Hz, 2H), 7.30 (t, J=4 Hz, 2H), 7.23 (m, 1H), 7.16 (dd, J=4 Hz, 2 Hz, 1H), 7.09 (s, 1H), 6.00 (s, 2H), 5.15 (s, 2H), 3.23 (m, 2H), 2.23 (t, J=6 Hz, 2H), 1.58 (m, 4H), 1.36 (m, 2H); MS (DCI/NH$_3$) m/e: 486 (M+H)$^+$.

N-(2,3-Methylenedioxy-6-benzyloxy-phenanthr-9-ylmethyl)-6-aminohexanoic acid (12). General procedures d & e from 10 (90%); white powder, recrystallized from EtOH to give white needles; mp 184-186° C.; $^1$H NMR (400.13 MHz) δ 7.90 (d, J=4 Hz, 1H), 7.87 (d, J=2 Hz, 1H), 7.77 (s, 1H), 7.60 (s, 1H), 7.44 (d, J=4 Hz, 2H), 7.34 (t, J=4 Hz, 2H), 7.30 (dd, J=4 Hz, 2 Hz, 1H), 7.28 (m, 1H), 7.16 (s, 1H), 6.03 (s, 2H), 5.19 (s, 2H), 4.46 (s, 2H), 2.83 (m, 2H), 2.26 (t, J=6 Hz, 2H), 1.90 (m, 2H), 1.68 (m, 2H), 1.28 (m, 2H); MS (DCI/NH$_3$) m/e: 472 (M+H)$^+$. Anal. (C$_{29}$H$_{29}$O$_5$N) C, H, N.

N-(2,3-Methylenedioxy-6-benzyloxy-phenanthr-9-ylmethyl)-5-aminohexanol (13) General procedure f from 10 (95%); white powder; mp 175-177° C.; $^1$H NMR (400.13 MHz) δ 7.90 (d, J=4 Hz, 1H), 7.86 (d, J=2 Hz, 1H), 7.76 (s, 1H), 7.45 (s, 1H), 7.44 (d, J=4 Hz, 2H), 7.32 (t, J=4 Hz, 2H), 7.26 (m, 1H), 7.24 (dd, J=4 Hz, 2 Hz, 1H), 7.14 (s, 1H), 6.03 (s, 2H), 5.22 (s, 2H), 4.24 (s, 2H), 3.53 (t, J=6 Hz, 2H), 2.72 (t, J=6 Hz, 2H), 1.58 (m, 2H), 1.47 (m, 2H), 1.29 (m, 4H); MS (DCI/NH$_3$) m/e: 458 (M+H)$^+$. Anal. (C$_{29}$H$_{31}$O$_4$N) C, H, N.

Methyl N-(2,3-methylenedioxy-6-benzyloxy-phenanthr-9-ylmethyl)-5-aminopentanoate (14). General procedure c from 7a (93%); colorless syrup; $^1$H NMR (400.13 MHz) δ 7.97 (d, J=4 Hz, 1H), 7.83 (d, J=2 Hz, 1H), 7.77 (s, 1H), 7.46 (s, 1H), 7.45 (d, J=4 Hz, 2H), 7.35 (t, J=4 Hz, 2H), 7.27 (m, 1H), 7.20 (dd, J=4 Hz, 2 Hz, 1H), 7.07 (s, 1H), 6.01 (s, 2H), 5.17 (s, 2H), 4.95 (s, 2H), 3.50 (s, 3H), 3.01 (m, 2H), 2.42 (t, J=6 Hz, 2H), 1.67 (m, 2H), 1.59 (m, 2H); MS (DCI/NH$_3$) m/e: 472 (M+H)$^+$.

N-(2,3-Methylenedioxy-6-benzyloxy-phenanthr-9-ylmethyl)-5-aminopentanoic acid (15). General procedures d & e from 10 (93%); white powder, recrystallized from EtOH to give white needles; mp 197-199° C.; $^1$H NMR (400.13 MHz) δ 7.89 (d, J=4 Hz, 1H), 7.88 (d, J=2 Hz, 1H), 7.77 (s, 1H), 7.46 (s, 1H), 7.45 (d, J=4 Hz, 2H), 7.34 (t, J=4 Hz, 2H), 7.29 (dd, J=4 Hz, 2 Hz, 1H), 7.27 (m, 1H), 7.16 (s, 1H), 6.05 (s, 2H), 5.21 (s, 2H), 4.42 (s, 2H), 2.89 (m, 2H), 2.27 (t, J=6 Hz, 2H), 1.89 (m, 2H), 1.68 (m, 2H); MS (DCI/NH$_3$) m/e: 458 (M+H)$^+$. Anal. (C$_{29}$H$_{27}$O$_5$N) C, H, N.

N-(2,3-Methylenedioxy-6-benzyloxy-phenanthr-9-ylcarbonyl)-L-proline (16). General procedures c & e from 7a (95%); white powder; mp 221-223° C.; $^1$H NMR (400.13 MHz) δ 8.00 (d, J=4 Hz, 1H), 7.85 (d, J=2 Hz, 1H), 7.81 (s, 1H), 7.46 (s, 1H), 7.45 (d, J=4 Hz, 2H), 7.36 (t, J=4 Hz, 2H), 7.30 (m, 1H), 7.23 (dd, J=4 Hz, 2 Hz, 1H), 7.13 (s, 1H), 6.04 (s, 2H), 5.19 (s, 2H), 4.71 (t, J=7 Hz, 1H), 3.62 (m, 2H), 2.21 (m, 2H), 1.83 (m, 2H); MS (DCI/NH$_3$) m/e: 470 (M+H)$^+$.

N-(2,3-Methylenedioxy-6-benzyloxy-phenanthr-9-ylmethyl)-L-proline methyl ester (17). General procedures c & d from 7a (85%); brown syrup; $^1$H NMR (400.13 MHz) δ 7.97 (d, J=4 Hz, 1H), 7.83 (d, J=2 Hz, 1H), 7.80 (s, 1H), 7.71 (s, 1H), 7.59 (d, J=4 Hz, 2H), 7.47 (t, J=4 Hz, 2H), 7.36 (m, 1H), 7.22 (dd, J=4 Hz, 2 Hz, 1H), 7.11 (s, 1H), 6.06 (s, 2H), 5.20 (s, 2H), 4.75 (s, 2H), 3.67 (s, 3H), 3.26 (d, J=17 Hz, 1H), 2.45 (m, 2H), 1.96 (m, 2H), 1.68 (m, 2H); MS (DCI/NH$_3$) m/e: 470 (M+H)$^+$.

N-(2,3-Methylenedioxy-6-benzyloxy-phenanthr-9-ylmethyl)-L-proline (18). General procedure e from 17 (100%); white powder; mp 147-149° C.; $^1$H NMR (400.13 MHz) δ 8.11 (d, J=4 Hz, 1H), 7.84 (d, J=2 Hz, 1H), 7.75 (s, 1H), 7.42 (s, 1H), 7.40 (d, J=4 Hz, 2H), 7.30 (t, J=4 Hz, 2H), 7.27 (m, 1H), 7.23 (dd, J=4 Hz, 2 Hz, 1H), 7.14 (s, 1H), 6.01 (s, 2H), 5.16 (s, 2H), 4.30 (s, 2H), 3.24 (m, 1H), 2.48 (m, 2H), 2.0 (m, 2H), 1.68 (m, 2H); MS (DCI/NH$_3$) m/e: 456 (M+H)$^+$. Anal. ($C_{28}H_{25}O_5N \cdot 1.0H_2O$) C, H, N.

N-(2,3-Methylenedioxy-6-benzyloxy-phenanthr-9-ylmethyl)-L-prolinol (19). General procedure f from 17 (95%); colorless oil, recrystallization from EtOH gave white powder; mp 122-124° C.; $^1$H NMR (400.13 MHz) δ 8.13 (d, J=4 Hz, 1H), 7.90 (d, J=2 Hz, 1H), 7.84 (s, 1H), 7.51 (d, J=4 Hz, 2H), 7.42 (s, 1H), 7.41 (t, J=4 Hz, 2H), 7.34 (m, 1H), 7.29 (dd, J=4 Hz, 2 Hz, 1H), 7.14 (s, 1H), 6.06 (s, 2H), 5.24 (s, 2H), 4.36 (d, J=7 Hz, 2H), 3.78 (d, J=17 Hz, 2H), 3.41 (m, 1H), 2.42 (m, 2H), 1.83 (m, 2H), 1.66 (m, 6H); MS (DCI/NH3) m/e: 442 (M+H)+. Anal. ($C_{28}H_{27}O_4N$) C, H, N.

N-(2,3-Methylenedioxy-6-benzyloxy-phenanthr-9-ylmethyl)-L-2-piperidinecarboxylic acid (20). General procedures c, d & e from 7a (83%); white powder; mp 168-170° C.; $^1$H NMR (400.13 MHz) δ 8.26 (d, J=4 Hz, 1H), 7.85 (d, J=2 Hz, 1H), 7.77 (s, 1H), 7.56 (s, 1H), 7.45 (d, J=4 Hz, 2H), 7.35 (t, J=4 Hz, 2H), 7.30 (m, 1H), 7.26 (dd, J=4 Hz, 2 Hz, 1H), 7.12 (s, 1H), 6.05 (s, 2H), 5.20 (s, 2H), 4.24 (s, 2H), 3.16 (m, 1H), 2.26 (m, 2H), 1.80 (m, 2H), 1.64 (m, 4H); MS (DCI/NH$_3$) m/e: 470 (M+H)$^+$. Anal. ($C_{29}H_{27}O_5N$) C, H, N.

N-(2,3-Methylenedioxy-6-benzyloxy-phenanthr-9-ylmethyl)-L-piperidinemethanol (21). General procedure f from 20 (95%); light brown oil, recrystallization from EtOH to gave white powder; mp 151-152° C.; $^1$H NMR (400.13 MHz) δ 8.17 (d, J=4 Hz, 1H), 7.89 (d, J=2 Hz, 1H), 7.83 (s, 1H), 7.51 (d, J=4 Hz, 2H), 7.43 (s, 1H), 7.40 (t, J=4 Hz, 2H), 7.34 (m, 1H), 7.27 (dd, J=4 Hz, 2 Hz, 1H), 7.14 (s, 1H), 6.06 (s, 2H), 5.23 (s, 2H), 4.45 (d, J=7 Hz, 2H), 3.46 (d, J=17 Hz, 2H), 2.85 (m, 1H), 2.37 (m, 2H), 1.69 (m, 6H); MS (DCI/NH$_3$) m/e: 456 (M+H)$^+$. Anal. ($C_{29}H_{29}O_4N$) C, H, N.

N-(2,3-Methylenedioxy-6-hydroxy-phenanthr-9-ylcarbonyl)-L-proline (22). General procedure g from 16 (92%); white powder; mp 230-231° C.; $^1$H NMR (400.13 MHz) δ 7.73 (d, J=4 Hz, 1H), 7.67 (s, 1H), 7.50 (d, J=2 Hz, 1H), 7.35 (s, 1H), 7.21 (dd, J=4 Hz, 2 Hz, 1H), 7.06 (m, 1H), 6.01 (s, 2H), 4.67 (t, J=7 Hz, 1H), 3.22 (m, 2H), 2.38 (m, 2H), 2.18 (m, 2H), 1.86 (m, 2H); MS (DCI/NH$_3$) m/e: 380 (M+H)$^+$.

N-(2,3-Methylenedioxy-6-hydroxy-phenanthr-9-ylmethyl)-L-proline (23). General procedure g from 18 (95%); white powder; mp 205-206° C.; $^1$H NMR (400.13 MHz) δ 8.07 (d, J=4 Hz, 1H), 7.82 (s, 1H), 7.80 (d, J=2 Hz, 1H), 7.42 (s, 1H), 7.21 (dd, J=4 Hz, 2 Hz, 1H), 7.10 (s, 1H), 6.04 (s, 2H), 4.09 (s, 2H), 3.16 (m, 1H), 2.38 (m, 2H), 2.23 (m, 2H), 1.95 (m, 2H); MS (DCI/NH$_3$) m/e: 366 (M+H)$^+$.

N-(2,3-Methylenedioxy-6-hydroxy-phenanthr-9-ylmethyl)-L-2-piperidinecarboxylic acid (24). General procedure g from 20 (95%); white powder; mp 211-213° C.; $^1$H NMR (400.13 MHz) δ 8.07 (d, J=4 Hz, 1H), 7.80 (s, 1H), 7.76 (d, J=2 Hz, 1H), 7.50 (s, 1H), 7.22 (dd, J=4 Hz, 2 Hz, 1H), 7.12 (s, 1H), 6.05 (s, 2H), 4.06 (s, 2H), 3.12 (m, 1H), 2.38 (m, 2H), 1.88 (m, 2H), 1.64 (m, 4H); MS (DCI/NH$_3$) m/e: 380 (M+H)$^+$.

N-(2,3-Methylenedioxy-6-methoxy-phenanthr-9-ylcarbonyl)-5-aminopentanoic acid (25). General procedures c & e from 7b (100%); white powder; mp 137-138° C.; $^1$H NMR (400.13 MHz) δ 7.92 (d, J=4 Hz, 1H), 7.82 (s, 1H), 7.75 (s, 1H), 7.71 (d, J=2 Hz, 1H), 7.13 (dd, J=4 Hz, 2 Hz, 1H), 7.09 (s, 1H), 6.00 (s, 2H), 3.89 (s, 3H), 3.23 (m, 2H), 2.23 (t, J=6 Hz, 2H), 1.58 (m, 4H); MS (DCI/NH$_3$) m/e: 412 (M+H)$^+$.

Methyl N-(2,3-Methylenedioxy-6-methoxy-phenanthr-9-ylmethyl)-5-aminopentanoate (26). General procedures c & d from 7b (90%); colorless syrup; $^1$H NMR (400.13 MHz) δ 8.10 (d, J=4 Hz, 1H), 7.82 (s, 1H), 7.70 (d, J=2 Hz, 1H), 7.52 (s, 1H), 7.12 (dd, J=4 Hz, 2 Hz, 1H), 7.08 (s, 1H), 6.04 (s, 2H), 3.89 (s, 3H), 3.80 (s, 2H), 3.56 (s, 3H), 2.80 (m, 2H), 2.33 (t, J=6 Hz, 2H), 1.64 (m, 4H); MS (DCI/NH$_3$) m/e: 396 (M+H)$^+$.

N-(2,3-Methylenedioxy-6-methoxy-phenanthr-9-ylmethyl)-5-aminopentanoic acid (27). General procedure e from 26 (99%); white powder; mp 145-146° C.; $^1$H NMR (400.13 MHz) δ 8.06 (d, J=4 Hz, 1H), 7.79 (s, 1H), 7.75 (d, J=2 Hz, 1H), 7.48 (s, 1H), 7.22 (dd, J=4 Hz, 2 Hz, 1H), 7.10 (s, 1H), 6.03 (s, 2H), 4.02 (s, 2H), 3.82 (s, 3H), 2.75 (m, 2H), 2.23 (t, J=6 Hz, 2H), 1.53 (m, 2H), 1.44 (m, 2H); MS (DCI/NH3) m/e: 382 (M+H)$^+$. Anal. ($C_{22}H_{23}O_5N$) C, H, N.

N-(2,3-Methylenedioxy-6-methoxy-phenanthr-9-ylmethyl)-5-aminopentanol (28) General procedure f from 27 (97%); colorless oil, recrystallization from EtOH gave white powder; mp 125-126° C.; $^1$H NMR (400.13 MHz) δ 8.00 (d, J=4 Hz, 1H), 7.76 (s, 1H), 7.72 (d, J=2 Hz, 1H), 7.44 (s, 1H), 7.13 (dd, J=4 Hz, 2 Hz, 1H), 7.05 (s, 1H), 6.04 (s, 2H), 3.95 (s, 2H), 3.93 (s, 3H), 3.58 (t, J=6 Hz, 2H), 2.75 (m, 2H), 1.55 (m, 2H), 1.44 (m, 2H), 1.30 (m, 2H); MS (DCI/NH$_3$) m/e: 368 (M+H)$^+$. Anal. ($C_{22}H_{25}O_4N$) C, H, N.

N-(2,3-Methylenedioxy-6-methoxy-phenanthr-9-ylcarbonyl)-L-proline (29). General procedures c & e from 7b (93%); white powder; mp 207-208° C.; $^1$H NMR (400.13 MHz) δ 7.78 (d, J=4 Hz, 1H), 7.70 (s, 1H), 7.54 (d, J=2 Hz, 1H), 7.35 (s, 1H), 7.20 (dd, J=4 Hz, 2 Hz, 1H), 7.14 (m, 1H), 6.01 (s, 2H), 4.67 (m, 1H), 3.90 (s, 3H), 3.22 (m, 2H), 2.38 (m, 2H), 1.86 (m, 2H); MS (DCI/NH$_3$) m/e: 394 (M+H)$^+$.

N-(2,3-Methylenedioxy-6-methoxy-phenanthr-9-ylmethyl)-L-proline methyl ester (30). General procedures c & d from 7a (85%); white syrup; $^1$H NMR (400.13 MHz) δ 8.20 (d, J=4 Hz, 1H), 7.80 (s, 1H), 7.70 (d, J=2 Hz, 1H), 7.52 (s, 1H), 7.21 (dd, J=4 Hz, 2 Hz, 1H), 7.13 (s, 1H), 6.05 (s, 2H), 4.02 (s, 2H), 3.89 (s, 3H), 3.67 (s, 3H), 3.14 (m, 1H), 2.32 (m, 2H), 2.14 (m, 2H), 1.86 (m, 2H); MS (DCI/NH$_3$) m/e: 394 (M+H)$^+$.

N-(2,3-Methylenedioxy-6-methoxy-phenanthr-9-ylmethyl)-L-proline (31). General procedure e from 30 (100%); white powder; mp 145-146° C.; $^1$H NMR (400.13 MHz) δ 8.21 (d, J=4 Hz, 1H), 7.77 (s, 1H), 7.72 (d, J=2 Hz, 1H), 7.56 (s, 1H), 7.23 (dd, J=4 Hz, 2 Hz, 1H), 7.10 (s, 1H), 6.04 (s, 2H), 4.05 (s, 2H), 3.96 (s, 3H), 3.16 (m, 1H), 2.36 (m, 2H), 2.14 (m, 2H), 1.81 (m, 2H); MS (DCI/NH$_3$) m/e: 380 (M+H)$^+$. Anal. ($C_{22}H_{21}O_5N$) C, H, N.

N-(2,3-Methylenedioxy-6-methoxy-phenanthr-9-ylmethyl)-L-prolinol (32). General procedure f from 31 (95%); white powder; mp 138-139° C.; $^1$H NMR (400.13 MHz) δ 8.16 (d, J=4 Hz, 1H), 7.88 (s, 1H), 7.80 (d, J=2 Hz, 1H), 7.46 (s, 1H), 7.23 (dd, J=4 Hz, 2 Hz, 1H), 7.14 (s, 1H), 6.07 (s, 2H), 4.03 (s, 2H), 3.94 (s, 3H), 3.70 (d, J=17 Hz, 2H), 3.16 (m, 1H), 2.38 (m, 2H), 2.23 (m, 2H), 1.95 (m, 2H); MS (DCI/NH$_3$) m/e: 366 (M+H)$^+$. Anal. ($C_{22}H_{23}O_4N$) C, H, N.

N-(2,3-Methylenedioxy-6-methoxy-phenanthr-9-ylmethyl)-L-2-piperidinecarboxylic acid (33). General procedures c, d & e from 7b (80%); white powder; mp 171-172° C.; $^1$H NMR (400.13 MHz) δ 8.21 (d, J=4 Hz, 1H), 7.75 (s, 1H), 7.72 (d, J=2 Hz, 1H), 7.56 (s, 1H), 7.23 (dd, J=4 Hz, 2 Hz, 1H), 7.10 (s, 1H), 6.04 (s, 2H), 4.08 (s, 2H), 3.96 (s, 3H), 3.08

(m, 1H), 2.38 (m, 2H), 1.84 (m, 2H), 1.60 (m, 4H); MS (DCI/NH$_3$) m/e: 394 (M+H)$^+$. Anal. (C$_{23}$H$_{23}$O$_5$N.2.0H$_2$O) C, H, N N-(2,3-Methylenedioxy-6-methoxy-phenanthr-9-ylmethyl)-L-2-piperidinemethanol (34). General procedure f from 33 (98%); white powder; mp 155-157° C.; $^1$H NMR (400.13 MHz) δ 8.16 (d, J=4 Hz, 1H), 7.88 (s, 1H), 7.80 (d, J=2 Hz, 1H), 7.47 (s, 1H), 7.22 (dd, J=4 Hz, 2 Hz, 1H), 7.15 (s, 1H), 6.07 (s, 2H), 4.06 (s, 2H), 3.98 (s, 3H), 3.68 (d, J=7 Hz, 2H), 2.87 (m, 1H), 2.40 (m, 2H), 1.64 (m, 6H); MS (DCI/NH$_3$) m/e: 380 (M+H)$^+$. Anal. (C$_{23}$H$_{25}$O$_4$N) C, H, N.

N-(2,3,6-Trimethoxyphenanthr-9-ylmethyl)-6-aminohexanoic acid (35). General procedures c, d & e from 7b (77%); brown powder; mp 133-134° C.; $^1$H NMR (400.13 MHz) δ 7.90 (d, J=4 Hz, 1H), 7.78 (s, 1H), 7.72 (d, J=2 Hz, 1H), 7.52 (s, 1H), 7.20 (dd, J=4 Hz, 2 Hz, 1H), 7.08 (s, 1H), 3.92 (s, 9H), 3.71 (s, 2H), 2.87 (m, 2H), 2.23 (m, 2H), 1.55 (m, 2H), 1.46 (m, 2H), 1.28 (m, 2H); MS (DCI/NH$_3$) m/e; 412 (M+H)$^+$.

N-(2,3,6-Trimethoxyphenanthr-9-ylmethyl)-5-aminohexanol (36). General procedure f from 35 (92%); yellow oil; $^1$H NMR (400.13 MHz) δ 7.88 (d, J=4 Hz, 1H), 7.76 (s, 1H), 7.71 (d, J=2 Hz, 1H), 7.44 (s, 1H), 7.13 (dd, J=4 Hz, 2 Hz, 1H), 7.05 (s, 1H), 5.99 (s, 2H), 3.94 (s, 9H), 3.80 (s, 2H), 3.73 (t, J=6 Hz, 2H), 2.75 (m, 2H), 1.50 (m, 4H), 1.28 (m, 4H); MS (DCI/NH$_3$) m/e: 398 (M+H)$^+$.

N-(2,3,6-Trimethoxyphenanthr-9-ylmethyl)-L-2-piperidinecarboxylic acid (37). General procedures c, d & e from 7c (75%); light yellow powder; mp 187-188° C.; $^1$H NMR (400.13 MHz) δ 8.21 (d, J=4 Hz, 1H), 7.78 (s, 1H), 7.71 (d, J=2 Hz, 1H), 7.56 (s, 1H), 7.23 (dd, J=4 Hz, 2 Hz, 1H), 7.10 (s, 1H), 4.10 (s, 2H), 3.98 (s, 9H), 3.12 (m, 1H), 2.42 (m, 2H), 1.80 (m, 2H), 1.60 (m, 4H); MS (DCI/NH$_3$) m/e: 410 (M+H)$^+$.

N-(2,3,6-Trimethoxyphenanthr-9-ylmethyl)-L-2-piperidinemethanol (38). General procedure f from 37 (95%); brown oil, recrystallization from EtOH gave yellow powder; mp 135-137° C.; $^1$H NMR (400.13 MHz) δ 8.21 (d, J=4 Hz, 1H), 7.78 (s, 1H), 7.72 (d, J=2 Hz, 1H), 7.50 (s, 1H), 7.20 (dd, J=4 Hz, 2 Hz, 1H), 7.14 (s, 1H), 6.07 (s, 2H), 4.10 (s, 2H), 3.96 (s, 9H), 3.74 (d, J=17 Hz, 2H), 2.87 (m, 1H), 2.41 (m, 2H), 1.66 (m, 6H); MS (DCI/NH$_3$) m/e: 396 (M+H)$^+$.

1-[3-(4,5-Dimethoxy-2-nitrophenyl)-2-(4-methoxyphenyl)-acryloyl]-pyrrolidine-2-carboxylic acid (39). General procedures c & e from 5b (90%); brown powder; mp 120-122° C.; $^1$H NMR (400.13 MHz) δ7.67 (s, 1H), 7.26 (d, J=4 Hz, 2H), 7.08 (s, 1H), 6.73 (d, J=4 Hz, 2H), 6.44 (s, 1H), 4.63 (t, J=7 Hz, 1H), 3.92 (s, 6H), 3.73 (s, 3H), 3.41 (t, J=7 Hz, 2H), 2.22 (m, 2H), 1.92 (m, 2H); MS (DCI/NH$_3$) m/e: 443 (M+H)$^+$.

1-[3-(4,5-Dimethoxy-2-nitrophenyl)-2-(4-methoxyphenyl)-allyl]-pyrrolidine-2-carboxylic acid (40)

General procedure d from 39 (90%); brown syrup; $^1$H NMR (400.13 MHz) δ 7.61 (s, 1H), 7.24 (d, J=4 Hz, 2H), 7.01 (s, 1H), 6.77 (d, J=4 Hz, 2H), 6.64 (s, 1H), 4.36 (d, J=7 Hz, 2H), 3.89 (s, 3H), 3.72 (t, J=7 Hz, 1H), 3.69 (s, 3H), 3.42 (s, 3H), 3.24 (m, 2H), 2.18 (m, 2H), 1.84 (m, 2H); MS (DCI/NH$_3$) m/e: 429 (M+H)$^+$.

{1-[3-(4,5-Dimethoxy-2-nitrophenyl)-2-(4-methoxyphenyl)-allyl]-pyrrolidin-2-yl}-methanol (41). General procedure f from 40 (90%); dark oil; $^1$H NMR (400.13 MHz) δ 7.59 (s, 1H), 7.23 (d, J=4 Hz, 2H), 7.00 (s, 1H), 6.71 (d, J=4 Hz, 2H), 6.23 (s, 1H), 4.17 (d, J=7 Hz, 2H), 3.89 (s, 3H), 3.78 (d, J=7 Hz, 2H), 3.69 (s, 3H), 3.58 (m, 1H), 3.41 (s, 3H), 3.16 (m, 2H), 1.91 (m, 2H), 1.80 (m, 2H); MS (DCI/NH$_3$) m/e: 415 (M+H)$^+$.

{1-[3-(3,4-Dimethoxyphenyl)-2-(4-methoxyphenyl)allyl]-pyrrolidin-2-yl}-methanol (42). Similar procedure as 40 (77% for two steps); yellow syrup; $^1$H NMR (400.13 MHz) δ 7.11 (d, J=5 Hz, 2H), 6.89 (d, J=5 Hz, 2H), 6.63 (s, 1H), 6.58 (d, J=3 Hz, 2H), 6.39 (s, 1H), 4.06 (d, J=7 Hz, 2H), 3.90 (d, J=6 Hz, 2H), 3.71 (s, 3H), 3.69 (s, 3H), 3.65 (m, 1H), 3.39 (s, 3H), 3.27 (m, 2H), 1.84 (m, 2H), 1.70 (m, 2H); MS (DCI/NH$_3$) m/e: 370 (M+H)$^+$.

Cell Growth Inhibition Assay. The human A549 lung cancer cell line was used for the cytotoxicity screening of PBT derivatives using the cell-based sulforhodamine B (SRB) microtitre plate assay. Compound stock solutions were prepared in DMSO with the final solvent concentration ≦2% DMSO (v/v), a concentration without effect on cell replication. The cells were cultured at 37° C. in RPMI-1640 supplemented with 25 mM N-2-hydroxyethylpiperazine-N'-2-ethanesulfonic acid (HEPES), 2% (w/v) sodium bicarbonate, 10% (v/v) fetal bovine serum, and 100 μg/mL kanamycin in a humidified atmosphere containing 5% CO$_2$. Duration of compound exposure was 3 days. The ED$_{50}$ value (the concentration that reduced the cell number by 50%) was interpolated from dose-response data. Each test was performed in triplicate with variation less than 5%. The ED$_{50}$ values determined in each independent test varied less than 10%.

See also Lebrun, S.; Couture, A.; Deniau, E.; Grandclaudon, P. Total syntheses of (±)cryptopleurine, (±)-antofine and (±)-deoxypergularinine. *Tetrahedron* 1999, 55, 2659-2670.

EXAMPLE 2

9-Substituted Phenanthren-Based Tylophorine Derivatives

Several N-containing cyclic and acyclic terminal-hydroxyl moieties were introduced at the C9 position in order to explore and optimize the activity profiles of novel C-9 substituted PBTs. Finally, the SAR is discussed relative to the current issues of chemotherapy-induced toxicity and resistance.

Chemistry. Compounds 13-36b were synthesized from commercially available 3,4-methylenedioxy-6-nitrobenzaldehyde and 4-methoxyphenylacetic acid according to the method described above. Briefly, 2,3-methylenedioxy-6-methoxy-phenanthrene-9-carboxylic acid (10) was obtained through a Perkin reaction (See, Wassmundt, F. W.; Kiesman, W. F., *J. Org. Chem.* 1995; 60:196-201; Lebrun, S et al., *Tetrahedron* 1999, 55, 2659-2670) and an improved freeradical Pschorr cyclization (Scheme 2) (Gellert, E. In Alkaloids: Chemical and Biological Perspectives; Pelletier, S. W. Ed.; Academic Press: New York, 1987; pp 55-132.) in a satisfactory overall yield of 78%.

Compound 10 was then condensed with the appropriate amines in the presence of N-(3-dimethylaminopropyl)-N-ethylcarbodiimide hydrochloride (EDC), 4-(dimethylamino) pyridine (DMAP) and 1-hydroxybenzotriazole (HOBT) (Scheme 3). The carbonyl bond of the amide was reduced with borane-methyl sulfide complex (BMS) to give the methylene amines and then the target carboxylic acid and hydroxymethyl analogs were produced by basic hydrolysis and lithium aluminum hydride (AlLiH$_4$) reduction, respectively.

TABLE 4
In vitro anticancer activity against A549 lung cancer cells.
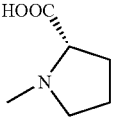
| Compound | R | A549 (μM) |
|---|---|---|
| 13 | —NH(CH$_2$)$_4$COOH | 1.3 |
| 14 | —NH(CH$_2$)$_4$CH$_2$OH | 0.27 |
| 15 | 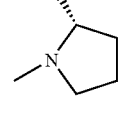 | 2.1 |
| 16 | 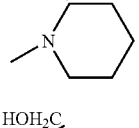 | 0.7 |
| 17 | 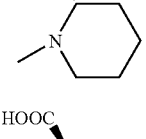 | 0.5 |
| 18a | 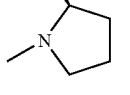 | 0.16 |
| 19 | 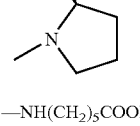 | 5.2 |
| 20 | 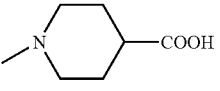 | 1.1 |
| 21 | —NH(CH$_2$)$_5$COOH | 0.8 |
| 22a | —NH(CH$_2$)$_5$CH$_2$OH | 0.2 |
| 23 | 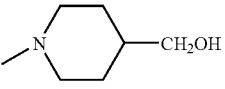 | 0.23 |
| 24a |  | 0.08 |
| 25 | —NH(CH$_2$)$_{10}$COOH | 3.2 |
| 26 | —NH(CH$_2$)$_{10}$CH$_2$OH | 2.6 |

TABLE 4-continued

In vitro anticancer activity against A549 lung cancer cells.

| Compound | R | A549 (μM) |
|---|---|---|
| 27 | (N-methylpiperazinyl)-(2-chlorophenyl) | NA |
| 28 | (N-methylpiperazinyl)-(4-chlorophenyl) | 65.2 |
| 29 | (N-methylpiperazinyl)-(4-hydroxyphenyl) | 0.22 |
| 30 | (N-methylpiperazinyl)-ethanol | 0.63 |
| 31 | (N-methylpiperazinyl)-ethoxyethanol | 57.1 |
| 32a | (N-methylpiperidinyl)-ethanol | 0.15 |
| Emetine | | 0.04 |
| Doxorubicin | | 0.18 |
| Etoposide(VP-16) | | 1.4 |
| Antofine | | 0.008 |
| Vincristine | | 0.04 |

Scheme 2

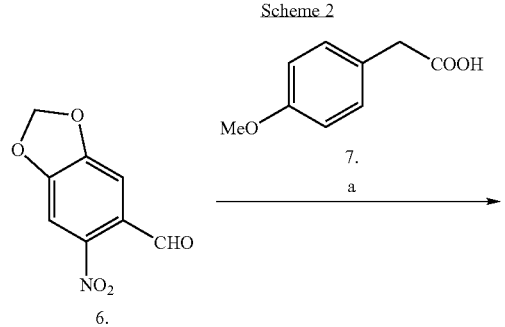

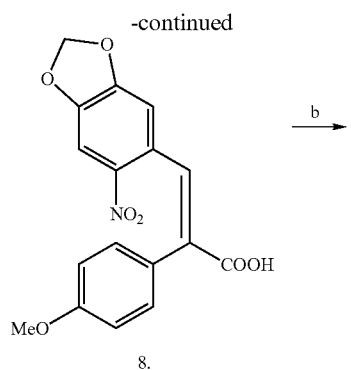

-continued

Reagents and conditions: a: Ac₂O/Et₃N b: FeSO₄/NH₄OH
c: NaNO₂/Fluoroboric acid; Ferrocene/acetone.

Scheme 3

Reagents and conditions: d; EDC, DMAP, HOBt/DMF
e: BMS/THF f: LiAlH₄/THF

Results and Discussion. The in vitro anticancer activity of target compounds (13-32b) was evaluated first against the human A549 lung cancer cell line using the cell-based sulforhodamine B (SRB) microtitre plate assay (Rubinstein, L. V.; Shoemaker, R. H.; Paull, K. D.; Simon, R. M.; Tosini, S.; Skehan, P.; Scudiero, D. A.; Monks, M. R. Comparison of in vitro anticancer-drug-screening data generated with a tetrazolium assay versus a protein assay against a diverse panel of Human tumor cell lines. *J. Natl. Cancer Inst.* 1990, 82, 1113-1118.). Compound structures and cytotoxic activity data against are shown in Table 4.

Twelve active compounds were further evaluated against three additional cancer cell lines (KB, DU145 and ZR-751) and one resistant subline (KB-Vin) (Table 5). Antofine, emetine, doxorubicin and etoposide (VP-16) were used as reference compounds.

TABLE 5

| Compound | R | A549 (µM) |
|---|---|---|
| 33 | HOOC- (N-methylpiperidin-2-yl) | 3.2 |
| 34 | HOH₂C- (N-methylpiperidin-2-yl) | 1.3 |
| 35 | N-methylpiperidin-4-yl-COOH | 2.1 |
| 36 | N-methylpiperidin-4-yl-CH₂OH | 0.7 |

Structure-Activity Relationship (SAR) Studies. Interestingly, changing the stereochemistry of the 2'-substituent on the pyrrole ring altered the potency. Compounds 15 and 16 were more potent than their stereoisomers 19 and 20. These findings are consistent with the earlier studies of tylophorine alkaloids that showed equal or higher cytotoxicity of the 13aS series as compared with the 13aR series (Abe, F. et al., *Chem. Pharm. Bull.* 1998, 46, 767-769.), suggesting a well-defined regioselective interaction of these compounds with the putative biological target.

For target compounds with varied acyclic N-containing side chains, the distance between the nitrogen and terminal substituent affected the potency. The aminoundecanoic acid analog was significantly less active than the corresponding aminopentanoic acid, which in turn was slightly less active than the aminohexanoic acid (25<13<21). A similar rank order of potency was found when the terminal carboxylic acid was reduced to a hydroxymethyl group (26<14<22a). The shorter spacing was definitely preferable to the longer spacing.

Based on the significant biological activity of the acylic amines, the position of the piperidine substituent was changed from 2' (ortho) to 4' (para), which resulted in increased potency (17 vs 23, 18a vs 24a), demonstrating that a terminal hydroxyl/carboxylic acid in a para position could favorably affect the activity. This conclusion was confirmed for compounds where the C-6 methoxy group was replaced with a benzyloxy ether (Table 2; 35 >33 and 36>34).

To investigate the relationship between activity and nitrogen content in the C-9 side chain, both piperidine (one nitrogen) and piperazine (two nitrogens) analogs were prepared and tested. Although the second nitrogen was tolerated, its presence slightly decreased activity [compare the $ED_{50}$ values between the piperazine-ethanol (30) and piperidine-ethanol (32a) analogs].

Additional SAR observations relative to the C-9 N-containing side chain were also noted in the course of our study. 4'-Hydroxymethyl and 4'hydroxyethylpiperidine analogs (24a and 32a, respectively) were both quite potent, but the former was more active than the latter. While the piperazine-ethanol analog (30) was quite active, the piperazine-ethoxyethanol analog (31) lost all activity. In contrast, potency was increased when the hydroxylethyl of 30 was replaced with a phenol in 29. These results corroborate the conclusion that an appropriate side chain length is important for maximal activity.

Since compound 29 was quite potent, while both ortho- and para-chlorophenyl substituted piperazine analogs (27, 28) were inactive, the presence of a hydrogen bond acceptor/donor group at C-9 chain terminus appears essential for cytotoxic activity. It could be that a hydrogen bonding interaction between the terminal group and a biological target plays an important role in binding the hypothetical target, and the spacing between this group and the remainder of the molecule needs to be well optimized.

Drug-Resistance Study. Twelve active compounds [including four hydrochloride salts (18b, 22b, 24b, 32b) of corresponding active free bases (18a, 22a, 24a, 32a)] were further screened against an extended panel of human tumor cell lines including DU-145 (prostate), ZR-751 (breast), KB (nasopharyngeal), and KB-VIN (multidug-resistant KB subline) in order to explore their antitumor spectra and drug-resistance profiles. Four compounds were used as reference compounds. Antofine is a positional isomer of tylophorine isolated from Asclepiadaceae by Dr. T. S. Wu in Taiwan (Wu, P. L. et al., *Heterocycles* 2002; 57:2401). Emetine is a protein synthesis inhibitor, which exhibits cross-resistance with tylocrebine in mutant CHO cells. Doxorubicin (Adriamycin), vincristine, and etoposide (VP-16, Vepesid®) are widely used anticancer agents for treating a range of solid tumors. The results are illustrated in Table 6. In general, all new compounds exhibited potent activity against KB ($ED_{50}$: 0.07-0.50 µM), DU-145 ($ED_{50}$: 0.03-0.67 µM), and ZR-751 ($ED_{50}$: 0.02-0.54 µM) cell lines, as well as KB-Vin ($ED_{50}$: 0.09-0.38 µM) cells. The corresponding salts showed similar selectivity pattern and slightly better potency than the free bases, possibly due to improved water solubility. Compared to the reference compounds emetine, doxorubicin, etoposide and vincristine, neither the C-9 substituted PBTs nor antofine showed any cross-resistance with the KB-Vin resistant cell line, suggesting that their mode may be distinctly different from that of other cancer chemotherapeutic compounds. All PBTs exhibited cytotoxic activity in the sub-micromolar range against the limited set of representative human cancer cell lines. Compound 22b was most active against DU-145 (prostate) and ZR-751 (breast) cancer cell lines, and compound 24b exhibited a fairly uniform and potent cytotoxic activity with $ED_{50}$ values less than 100 nM against the tumor cell line panel. Compound 32a and its HCl salt (32b) were most active against ZR-751 breast cancer cell replication.

TABLE 6

| Compound | $EC_{50}$ (µM) | | | | |
|---|---|---|---|---|---|
| | A549 | KB | DU-145 | ZR-751 | KB-VIN |
| 18a | 0.2 | 0.12 | 0.21 | 0.1 | 0.16 |
| 18b | 0.16 | 0.12 | 0.09 | 0.08 | 0.09 |
| 21 | 0.5 | 0.33 | 0.67 | 0.54 | 0.83 |
| 22a | 0.16 | 0.25 | 0.04 | 0.13 | 0.35 |
| 22b | 0.13 | 0.23 | 0.07 | 0.08 | 0.16 |
| 23 | 0.23 | 0.15 | 0.31 | 0.25 | 0.38 |
| 24a | 0.08 | 0.24 | 0.03 | 0.03 | 0.09 |
| 24b | 0.07 | 0.07 | 0.05 | 0.04 | 0.04 |
| 29 | 0.22 | 0.13 | 0.15 | 0.18 | 0.34 |
| 30 | 0.63 | 0.50 | 0.25 | 0.23 | 0.51 |
| 32a | 0.15 | 0.42 | 0.15 | 0.03 | 0.50 |
| 32b | 0.09 | 0.20 | 0.1 | 0.02 | 0.20 |
| Antofine | 0.008 | 0.013 | 0.009 | 0.008 | 0.009 |
| Emetine | 0.04 | 0.04 | 0.06 | 0.1 | >2 |
| Doxorubicin | 0.18 | 0.18 | 0.13 | 0.04 | >4 |
| Etoposide (VP-16) | 1.4 | 4.8 | 2.4 | 3.1 | >10 |
| Vincristine | 0.04 | 0.006 | 0.085 | 0.04 | 5.3 |

Conclusions. A series of novel 9-substituted 2,3-methylenedioxy-6-methoxy-PBTs were synthesized and exhibited potent cytotoxic activity against a limited but diverse panel of human tumor cell lines, including a multidrug-resistant variant. The $EC_{50}$ values were in the sub-micromolar range, comparable with the activity of the two front-line antineoplastic drugs used as positive controls, and the new compounds had a superior drug-resistance profile. Combination of a 2,3-methylenedioxy-6-methoxyphenanthrene skeleton with a C-9 cyclic piperidine ring and para terminal hydroxyl side chain generated the most potent PBTs. N-(2,3-Methylenedioxy-6-methoxy-phenanthr-9-ylmethyl)-L-4-piperidinemethanol (24a) exhibited a fairly uniform and potent cytotoxic activity with $ED_{50}$ values less than 100 nM against the cell line panel. The activity was maintained and the water solubility increased by formation of the hydrochloride salt (24b). These PBT salts are the first reported water soluble tylophorine derivatives with significant cytotoxic activity, in particular to multidrug-resistant cells. They represent well-qualified and promising clinical trial candidates for cancer (especially refractory cancer) treatment.

Experimental section. Melting points were measured using Fisher Johns melting apparatus without correction. The proton nuclear magnetic resonance (¹H NMR) spectra were measured on a 300 MHz Varian Gemini 2000 spectrometer using TMS as internal standard. Mass spectra were recorded on a PE-Sciex API-3000 LC/MS/MS instrument equipped with a Turbo IonsSpray ion source. The solvent used was $CDCl_3$ unless indicated. Elemental analyses were performed by Atlantic Microlab, Inc., Norcross, Ga. All target compounds were analyzed for C, H, N and gave values within +/−4% of the theoretical values. Thin-layer chromatography (TLC) was performed on PLC silica gel 60 $F_{254}$ plates (0.5 mm, Merck). Biotage Flash+ and Isco Companion systems were used as medium-pressure column chromatography. Silica gel (200-400 mesh) from Aldrich, Inc., was used for column chromatography. 4-benzyloxyphenylacetic acid and 3,4-Methylenedioxy-6-nitrobenzaldehyde were purchased from TCI. Isonipecolic acid and L-pipecolinic acid were commercially available from Lancaster. All other chemicals were obtained from Aldrich, Inc. and Fisher, Inc.

General preparation. A solution of 3,4-methylenedioxy-6-nitrobenzaldehyde (12 mmol), $NEt_3$ (12 mmol), 4-methoxyphenylacetic acid (17 mmol) was refluxed with stirring under Ar for 40 min. [20] Water (30 ml) was added to the reaction mixture and during the addition the temperature was maintained between 90° C. and 100° C. The reaction mixture was cooled to ambient temperature and solid was collected by filtration and recrystallized from EtOH.

4,5-Methylenedioxy-(4-methoxyphenyl)-2-nitrocinnamic acid (8). 91% yield; yellow powder; mp 184-185° C.; ¹H NMR (400.13 MHz) δ 7.92 (s, 1H), 7.53 (s, 1H), 7.01 (d, J=2 Hz, 2H), 6.73 (d, J=2 Hz, 2H), 6.22 (s, 1H), 5.96 (s, 2H), 3.74 (s, 3H); MS ($DCI/NH_3$) m/e: 344 $(M+H)^+$.

To a solution of the acid (7 mmol) in 10% aqueous $NH_4OH$ (100 ml) was added ferrous sulfate heptahydrate (15 g) dissolved in distilled water (100 ml) and concentrated aqueous $NH_4OH$ (100 ml). The reaction mixture was refluxed for 1.5 h, cool to 40° C. and filtrate on Celite and acidified with acetic acid (100 ml), the solid was collected by filtration and recrystallization from EtOH yielded the aminostilbenic acid.

4,5-Methylenedioxy-(4-methoxyphenyl)-2-aminocinnamic acid (9). 95% yield; yellow powder; mp 165-166° C.; ¹H NMR (400.13 MHz) δ 7.74 (s, 1H), 7.08 (d, J=2 Hz, 2H), 6.80 (d, J=2 Hz, 2H), 6.17 (s, 1H), 6.06 (s, 1H), 5.70 (s, 2H), 3.80 (s, 2H), 3.73 (s, 3H); MS ($DCI/NH_3$) m/e: 314 $(M+H)^+$.

A solution composed of the aminostilbenic acid (3 mmol), NaOH (33 mmol) and $NaNO_2$ in water (10 ml) was added dropwise over 30 min with stirring to 48% fluoroboric acid (43 mmol) at 0-5° C. The mixture was stirred for 1 h after which sulfamic acid was added until the mixture tested negative to starch-iodide paper. The crude solid was collected by filtration, dissolved in anhydrous acetone (10 ml) and then added dropwise with stirring over a 15 min period to ferrocene (0.056 g, 0.3 mmol) in acetone at ambient temperature. After an additional 15 min of stirring the green reaction mixture was added to water (100 ml). A light-yellow precipitate was collected and the trace amount of ferrocene was removed in vacuo to afford the phenanthroic acid.

2,3-Methylenedioxy-6-methoxy-phenanthrene-9-carboxylic acid (10). 92% yield; white powder; mp 293-295° C.; ¹H NMR (400.13 MHz) δ 7.67 (s, 1H), 7.60 (d, J=4 Hz, 1H), 7.22 (dd, J=4 Hz, 2 Hz, 1H), 6.92 (s, 1H), 6.89 (d, J=2 Hz, 1H), 6.70 (s, 1H), 5.98 (s, 2H), 3.79 (s, 3H); MS (DCI/NH3) m/e: 297 $(M+H)^+$.

General Procedure for the protection of cycloalkylamino acid: To a solution of cycloalkylamino acid (4 mmol) in dry MeOH (4 ml) was added dropwise $SOCl_2$ (0.4 ml) at −30° C. The reaction mixture was warmed to room temperature and refluxed for 1 h. Then the solvent was removed in vacuo and the product was used in the next reaction without any further purification.

General Procedure for the protection of acyclic alkylamino acid: To a solution of dry MeOH (3 ml) was added dropwise AcCl (0.45 ml) at 0° C. After 10 min stirring, the amino acid was added to the solution in portions. The mixture was warmed to room temperature and refluxed for 2 h, then the solvent was removed in vacuo and the product was used in the next reaction without any further purification.

General Procedure for the peptide bond condensation reaction (a): To a solution of phenanthroic acid (4 mmol), 4-(dimethylamino) pyridine (DMAP) (2 mmol), 1-hydroxybenzotriazole (HOBT) (4 mmol) and methyl protected amino acid (4.4 mmol) in 20 ml DMF was added NMM (1.03 ml). The mixture was stirring at 0° C. for 15 min, N-(3-dimethylaminopropyl)-N'-ethylcarbodiimide hydrochloride (EDC) (4.4 mmol) was added by portion. The reaction mixture was stirred overnight at room temperature and partitioned between EtOAc and water. The organic layer was washed with brine, saturated $NaHCO_3$ and 1N HCl, dried over $Na_2SO_4$, and concentrated in vacuo. The crude product was chromatographed using Biotage Flash+ and Isco Companion systems using a 40 g silica cartridge and EtOAc/hexane as eluant.

General Procedure for the carbonyl reduction reaction (b): To a stirred solution of 9-ylcarbonyl compound (2 mmol) in THF (20 ml) was added dropwise borane-methyl sulfide (BMS) (4 ml, 2.0M solution in THF), the reaction was stirred at room temperature overnight and quenched with 1N HCl. THF was removed in vacuo. The residue was partitioned between $CH_2Cl_2$ and water. The organic layer was dried, filtered and evaporated to afford 9-ylmethyl ester. The crude product was chromatographed using Biotage Flash+ and Isco Companion systems using $MeOH/CH_2Cl_2$ as eluant.

General Procedure for the basic hydrolysis reaction (c): A solution of ester, 4N NaOH and MeOH (1:1) was refluxed for 4 h. The reaction mixture was acidified and partitioned between 10% $MeOH/CH_2Cl_2$ and 1N HCl, The organic layer was dried over $Na_2SO_4$, filtered and evaporated. The crude product was chromatographed using Biotage Flash+ and Isco Companion systems using $MeOH/CH_2Cl_2$ as eluant.

General Procedure for the $AlLiH_4$ reduction (d): To a suspension of methyl ester (1 mmol) in 15 ml dry THF was added $LiAlH_4$ (1 g) in portions at 0° C. After addition, the reaction mixture was refluxed for 4 h, and then cooled to 0° C. The reaction mixture was quenched with methnol, and then 10% Rochelle salt was added. The reaction mixture was extracted with water and 10% $MeOH/CH_2Cl_2$. The organic layer was dried over $Na_2SO_4$, and the crude product was chromatographed using Biotage Flash+ and Isco Companion systems using $MeOH/CH_2Cl_2$ as eluant. The product was partitioned between water and 10% $MeOH/CH_2Cl_2$. Organic layer was dried over $Na_2SO_4$, and the crude product was chromatographed using Biotage Flash+ and Isco Companion systems using $MeOH/CH_2Cl_2$ as eluant.

General Procedure for making hydrochloride salt (e): To a suspension of the free base (3 mmol) in EtOH (15 ml) was added dropwise an equivalent of 6N HCl. After the free base was well dissolved, the solvent was removed in vacuo and the remaining hydrochloride salt was dried over phosphorus pentoxide.

The physical and spectral data for 13-18a and 33, 34 have been described above.

N-(2,3-Methylenedioxy-6-methoxy-phenanthr-9-ylmethyl)-L-2-piperidinemethanol hydrochloride (18b). mp 193-194° C.; ¹H NMR (400.13 MHz) δ 8.14 (d, J=4 Hz, 1H), 8.00

(s, 1H), 7.78 (d, J=2 Hz, 1H), 7.49 (s, 1H), 7.20 (dd, J=4 Hz, 2 Hz, 1H), 7.15 (s, 1H), 6.04 (s, 2H), 4.20 (s, 2H), 3.90 (s, 3H), 3.72 (d, J=17 Hz, 2H), 3.04 (m, 1H), 2.68 (m, 2H), 1.83 (m, 6H); MS (DCI/NH$_3$) m/e: 380 (M+H)$^+$. Anal. (C$_{23}$H$_{25}$O$_4$N.1.0HCl.2.0H$_2$O) C, H, N, N-(2,3-Methylenedioxy-6-methoxy-phenanthr-9-ylmethyl)-D-proline (19). General procedures a, b & c from 10 (81%); white powder; p 152-153° C.; $^1$H NMR (400.13 MHz) δ 8.21 (d, J=4 Hz, 1H), 7.77 (s, 1H), 7.72 (d, J=2 Hz, 1H), 7.56 (s, 1H), 7.23 (dd, J=4 Hz, 2 Hz, 1H), 7.10 (s, 1H), 6.04 (s, 2H), 4.05 (s, 2H), 3.96 (s, 3H), 3.16 (m, 1H), 2.36 (m, 2H), 2.14 (m, 2H), 1.81 (m, 2H); MS (DCI/NH$_3$) m/e: 380 (M+H)$^+$. Anal. (C$_{22}$H$_{21}$O$_5$N) C, H, N.

N-(2,3-Methylenedioxy-6-methoxy-phenanthr-9-ylmethyl)-D-prolinol (20). General procedure d from 19 (95%); yellow syrup, recrystallization from EtOH gave white powder; mp 130-132° C.; $^1$H NMR (400.13 MHz) δ 8.16 (d, J=4 Hz, 1H), 7.88 (s, 1H), 7.80 (d, J=2 Hz, 1H), 7.46 (s, 1H), 7.23 (dd, J=4 Hz, 2 Hz, 1H), 7.14 (s, 1H), 6.07 (s, 2H), 4.03 (s, 2H), 3.94 (s, 3H), 3.70 (d, J=17 Hz, 2H), 3.16 (m, 1H), 2.38 (m, 2H), 2.23 (m, 2H), 1.95 (m, 2H); MS (DCI/NH$_3$) m/e: 366 (M+H)$^+$. Anal. (C$_{22}$H$_{23}$O$_4$N) C, H, N.

N-(2,3-Methylenedioxy-6-methoxy-phenanthr-9-ylmethyl)-6-aminohexanoic acid (21) General procedures a, b & c from 10 (78%); white powder; mp 167-169° C.; $^1$H NMR (400.13 MHz) δ 7.88 (d, J=4 Hz, 1H), 7.76 (s, 1H), 7.71 (d, J=2 Hz, 1H), 7.44 (s, 1H), 7.13 (dd, J=4 Hz, 2 Hz, 1H), 7.05 (s, 1H), 5.99 (s, 2H), 3.87 (s, 2H), 3.82 (s, 3H), 2.75 (m, 2H), 2.23 (t, J=6 Hz, 2H), 1.53 (m, 2H), 1.44 (m, 2H), 1.28 (m, 2H); MS (DCI/NH$_3$) m/e: 396 (M+H)$^+$. Anal. (C$_{23}$H$_{25}$O$_5$N) C, H, N.

N-(2,3-Methylenedioxy-6-methoxy-phenanthr-9-ylmethyl)-6-aminohexanol (22a). General procedure d from 21 (90%); light green syrup, recrystallization from EtOH gave pale green powder; mp 145-147° C.; $^1$H NMR (400.13 MHz) δ 7.90 (d, J=4 Hz, 1H), 7.84 (s, 1H), 7.78 (d, J=2 Hz, 1H), 7.51 (s, 1H), 7.21 (dd, J=4 Hz, 2 Hz, 1H), 7.14 (s, 1H), 6.03 (s, 2H), 4.34 (s, 2H), 3.94 (s, 3H), 3.48 (t, J=6 Hz, 2H), 2.76 (m, 2H), 1.58 (m, 2H), 1.45 (m, 2H, 1.26 (m, 2H), 1.20 (m, 2H); MS (DCI/NH$_3$) m/e: 382 (M+H)$^+$. Anal. (C$_{23}$H$_{27}$O$_4$N) C, H, N.

N-(2,3-Methylenedioxy-6-methoxy-phenanthr-9-ylmethyl)-6-aminohexanol hydrochloride (22b) White powder; mp 187-188° C.; $^1$H NMR (400.13 MHz) δ 8.14 (d, J=4 Hz, 1H), 7.82 (s, 1H), 7.76 (d, J=2 Hz, 1H), 7.50 (s, 1H), 7.18 (dd, J=4 Hz, 2 Hz, 1H), 7.13 (s, 1H), 6.08 (s, 2H), 4.67 (s, 2H), 3.98 (s, 3H), 3.60 (t, J=6 Hz, 2H), 3.44 (m, 2H), 1.66 (m, 2H), 1.59 (m, 2H), 1.40 (m, 2H), 1.33 (m, 2H); MS (DCI/NH$_3$) m/e: 382 (M+H)$^+$. Anal. (C$_{23}$H$_{27}$O$_4$N.1.0HCl.1.5H$_2$O) C, H, N.

N-(2,3-Methylenedioxy-6-methoxy-phenanthr-9-ylmethyl)-L-4-piperidinecarboxylic acid (23). General procedures a, b & c from 10 (85%); light yellow powder; mp 238-240° C.; $^1$H NMR (400.13 MHz) δ 8.30 (d, J=4 Hz, 1H), 7.92 (s, 1H), 7.83 (d, J=1 Hz, 1H), 7.42 (s, 1H), 7.22 (dd, J=4 Hz, 2,4 Hz, 1H), 7.17 (s, 1H), 6.09 (s, 2H), 4.04 (s, 2H), 3.66 (s, 3H), 2.98 (m, 1H), 2.58 (m, 4H), 1.75 (m, 4H); MS (DCI/NH$_3$) m/e: 394 (M+H)$^+$. Anal. (C$_{23}$H$_{23}$O$_5$N) C, H, N.

N-(2,3-Methylenedioxy-6-methoxy-phenanthr-9-ylmethyl)-L-4-piperidinemethanol (24a). General procedure d from 23 (92%); light green syrup, recrystallization from EtOH gave white powder; mp 130-132° C.; $^1$H NMR (400.13 MHz) δ 8.26 (d, J=4 Hz, 1H), 7.87 (s, 1H), 7.78 (d, J=2 Hz, 1H), 7.38 (s, 1H), 7.19 (dd, J=4 Hz, 2 Hz, 1H), 7.14 (s, 1H), 6.05 (s, 2H), 3.97 (s, 3H), 3.81 (s, 2H), 3.43 (d, J=7 Hz, 2H), 2.97 (m, 2H), 2.02 (m, 2H), 1.65 (m, 2H), 1.48 (m, 1H), 1.26 (m, 2H); MS (DCI/NH$_3$) m/e: 380 (M+H)$^+$. Anal. (C$_{23}$H$_{25}$O$_4$N) C, H, N.

N-(2,3-Methylenedioxy-6-methoxy-phenanthr-9-ylmethyl)-L-4-piperidinemethanol hydrochloride (24b). White powder; mp 256-258° C.; $^1$H NMR (400.13 MHz) δ 8.00 (d, J=4 Hz, 1H), 7.85 (s, 1H), 7.82 (s, 1H), 7.77 (d, J=2 Hz, 1H), 7.22 (dd, J=4 Hz, 2 Hz, 1H), 7.20 (s, 1H), 6.03 (d, J=4 Hz, 2H), 4.59 (s, 2H), 3.92 (s, 3H), 3.46 (d, J=4 Hz, 2H), 3.31 (m, 2H), 2.77 (m, 2H), 1.76 (m, 4H), 1.68 (m, 1H); MS (DCI/NH$_3$) m/e: 380 (M+H)$^+$. Anal. (C$_{23}$H$_{25}$O$_4$N.1.0HCl.1.0H$_2$O) C, H, N.

N-(2,3-Methylenedioxy-6-methoxy-phenanthr-9-ylmethyl)-11-aminoundecanoic acid (25). General procedures a, b & c from 10 (75%); white powder; mp 146-148° C.; $^1$H NMR (400.13 MHz) δ 7.98 (d, J=4 Hz, 1H), 7.80 (s, 1H), 7.72 (d, J=2 Hz, 1H), 7.50 (s, 1H), 7.11 (dd, J=4 Hz, 2 Hz, 1H), 7.06 (s, 1H), 6.05 (s, 2H), 4.02 (s, 3H), 3.86 (s, 2H), 2.93 (m, 2H), 2.2 (m, 2H), 1.67 (m, 2H), 1.53 (m, 2H), 1.21 (m, 12H); MS (DCI/NH$_3$) m/e: 466 (M+H)$^+$. Anal. (C$_{28}$H$_{35}$O$_5$N) C, H, N.

N-(2,3-Methylenedioxy-6-methoxy-phenanthr-9-ylmethyl)-6-aminoundecanol (26). General procedure d from 21 (90%); light green syrup, recrystallization from EtOH gave pale green powder; mp 122-124° C.; $^1$H NMR (400.13 MHz) δ 7.86 (d, J=4 Hz, 1H), 7.67 (s, 1H), 7.40 (d, J=2 Hz, 1H), 7.43 (s, 1H), 7.18 (dd, J=4 Hz, 2 Hz, 1H), 7.08 (s, 1H), 6.01 (s, 2H), 4.32 (s, 2H), 3.88 (s, 3H), 3.68 (t, J=6 Hz, 2H), 2.86 (m, 2H), 1.68 (m, 2H), 1.58 (m, 2H), 1.26 (m, 14H); MS (DCI/NH$_3$) m/e: 452 (M+H)$^+$. Anal. (C$_{28}$H$_{37}$O$_4$N) C, H, N. N-(2,3-Methylenedioxy-6-methoxy-phenanthr-9-ylmethyl)-(4-chlorophenyl)-piperazine (27). General procedures a & d from 10 (87%); white powder; mp 196-198° C.; $^1$H NMR (400.13 MHz) δ 8.32 (d, J=4 Hz, 1H), 7.91 (s, 1H), 7.81 (d, J=2 Hz, 1H), 7.44 (s, 1H), 7.32 (dd, J=4 Hz, 2 Hz, 1H), 7.22 (d, J=9 Hz, 1H), 7.18 (s, 1H), 7.16 (d, J=9 Hz, 1H), 7.00 (m, 1H), 6.93 (m, 1H), 6.08 (s, 2H), 4.30 (s, 2H), 3.94 (s, 3H), 3.68 (t, J=6 Hz, 4H), 3.05 (m, 4H); MS (DCI/NH$_3$) m/e: 461.5 (M+H)$^+$. Anal. (C$_{27}$H$_{25}$O$_3$N$_2$Cl) C, H, N.

N-(2,3-Methylenedioxy-6-methoxy-phenanthr-9-ylmethyl)-(2-chlorophenyl)-piperazine (28). General procedures a & d from 10 (80%); white powder; mp 222-223° C.; $^1$H NMR (400.13 MHz) δ 8.30 (d, J=4 Hz, 1H), 7.90 (s, 1H), 7.81 (d, J=2 Hz, 1H), 7.50 (s, 1H), 7.22 (dd, J=4 Hz, 2 Hz, 1H), 7.19 (s, 1H), 7.17 (d, J=9 Hz, 2H), 6.89 (d, J=9 Hz, 2H), 6.09 (s, 2H), 4.68 (s, 2H), 3.90 (s, 3H), 3.65 (t, J=8 Hz, 4H), 3.14 (m, 4H); MS (DCI/NH$_3$) m/e: 461.5 (M+H)$^+$. Anal. (C$_{27}$H$_{25}$O$_3$N$_2$Cl) C, H, N.

N-(2,3-Methylenedioxy-6-methoxy-phenanthr-9-ylmethyl)-(4-hydroxyphenyl)-piperazine (29). General procedures a & d from 10 (82%); white powder; mp 225-227° C.; $^1$H NMR (400.13 MHz) δ 8.10 (d, J=4 Hz, 1H), 7.90 (s, 1H), 7.82 (d, J=2 Hz, 1H), 7.49 (s, 1H), 7.22 (dd, J=4 Hz, 2 Hz, 1H), 7.14 (s, 1H), 6.76 (d, J=9 Hz, 2H), 6.61 (d, J=9 Hz, 2H), 6.12 (s, 2H), 4.43 (s, 2H), 3.85 (s, 3H), 3.21 (t, J=8 Hz, 4H), 2.83 (m, 4H); MS (DCI/NH$_3$) m/e: 443 (M+H)$^+$. Anal. (C$_{27}$H$_{26}$O$_4$N$_2$) C, H, N.

N-(2,3-Methylenedioxy-6-methoxy-phenanthr-9-ylmethyl)-N-(2-hydroxyethyl)-piperazine (30). General procedures a & d from 10 (86%); white powder; mp 142-144° C.; $^1$H NMR (400.13 MHz) δ 8.18 (d, J=4 Hz, 1H), 7.85 (s, 1H), 7.76 (d, J=2 Hz, 1H), 7.32 (s, 1H), 7.16 (dd, J=4 Hz, 2 Hz, 1H), 7.10 (s, 1H), 6.05 (s, 2H), 3.96 (s, 3H), 3.82 (s, 2H), 3.70 (t, J=6 Hz, 2H), 2.70 (m, 8H), 2.61 (m, 2H); MS (DCI/NH$_3$) m/e: 395 (M+H)$^+$. Anal. (C$_{23}$H$_{26}$O$_4$N$_2$) C, H, N.

N-(2,3-Methylenedioxy-6-methoxy-phenanthr-9-ylmethyl)-(2-hydroxyethylethoxy)-piperazine (31). General procedures a & d from 10 (78%); white powder; mp 145-147° C.; $^1$H NMR (400.13 MHz) δ 8.10 (d, J=4 Hz, 1H), 7.80 (s, 1H), 7.75 (d, J=2 Hz, 1H), 7.46 (s, 1H), 7.14 (dd, J=4 Hz, 2 Hz, 1H), 7.09 (s, 1H), 6.05 (s, 2H), 3.96 (s, 3H), 3.89 (s, 2H), 3.79 (t, J=6 Hz, 2H), 3.61 (t, J=6 Hz, 2H), 3.49 (t, J=6 Hz, 2H), 3.12 (m, 8H), 2.87 (m, 2H); MS (DCI/NH$_3$) m/e: 439 (M+H)$^+$. Anal. (C$_{25}$H$_{30}$O$_5$N$_2$) C, H, N.

N-(2,3-Methylenedioxy-6-methoxy-phenanthr-9-ylm-ethyl)-4-piperidineethanol (32a) General procedures a & d from 10 (88%); white powder; mp 148-149° C.; $^1$H NMR (400.13 MHz) δ 8.08 (d, J=4 Hz, 1H), 7.90 (s, 1H), 7.81 (d, J=2 Hz, 1H), 7.45 (s, 1H), 7.22 (dd, J=4 Hz, 2 Hz, 1H), 7.17 (s, 1H), 6.09 (s, 2H), 4.14 (s, 2H), 3.98 (s, 3H), 3.52 (t, J=6 Hz, 2H), 3.00 (m, 2H), 2.58 (m, 2H), 1.65 (m, 4H), 1.55 (m, 1H), 1.43 (m, 2H); MS (DCI/NH$_3$) m/e: 394 (M+H)$^+$. Anal. (C$_{24}$H$_{27}$O$_4$N) C, H, N.

N-(2,3-Methylenedioxy-6-methoxy-phenanthr-9-ylm-ethyl)-4-piperidineethanol hydrochloride (32b). White powder; mp 153-155° C.; $^1$H NMR (400.13 MHz) δ δ 8.07 (d, J=4 Hz, 1H), 7.94 (s, 1H), 7.83 (d, J=2 Hz, 1H), 7.50 (s, 1H), 7.22 (dd, J=4 Hz, 2 Hz, 1H), 7.15 (s, 1H), 6.10 (s, 2H), 4.56 (s, 2H), 3.98 (s, 3H), 3.56 (t, J=6 Hz, 2H), 3.44 (m, 2H), 2.84 (m, 2H), 1.85 (m, 4H), 1.73 (m, 1H), 1.45 (m, 2H); MS (DCI/NH$_3$) m/e: 394 (M+H)$^+$. Anal. (C$_{24}$H$_{27}$O$_4$N.1.0HCl.2.0H$_2$O) C, H, N.

N-(2,3-Methylenedioxy-6-benzyloxy-phenanthr-9-ylm-ethyl)-L-4-piperidinecarboxylic acid (35). Similar procedure as 23 (77% for a, b and c); white powder; mp 183-185° C.; $^1$H NMR (400.13 MHz) δ 8.05 (d, J=4 Hz, 1H), 7.89 (d, J=2 Hz, 1H), 7.81 (s, 1H), 7.52 (d, J=4 Hz, 2H), 7.43 (s, 1H), 7.40 (t, J=4 Hz, 2H), 7.33 (m, 1H), 7.26 (dd, J=4 Hz, 2 Hz, 1H), 7.15 (s, 1H), 6.08 (s, 2H), 5.26 (s, 2H), 3.92 (s, 2H), 2.89 (m, 1H), 2.36 (m, 4H), 1.83 (m, 4H); MS (DCI/NH$_3$) m/e: 470 (M+H)$^+$. Anal. (C$_{29}$H$_{27}$O$_5$N) C, H, N.

N-(2,3-Methylenedioxy-6-benzyloxy-phenanthr-9-ylm-ethyl)-L-4-piperidinemethanol (36). General procedure d from 35 (93%); white powder; mp 120-122° C.; $^1$H NMR (400.13 MHz) δ 8.25 (d, J=4 Hz, 1H), 7.89 (d, J=2 Hz, 1H), 7.84 (s, 1H), 7.51 (d, J=4 Hz, 2H), 7.44 (t, J=4 Hz, 2H), 7.33 (m, 1H), 7.26 (dd, J=4 Hz, 2 Hz, 1H), 7.15 (s, 1H), 6.07 (s, 2H), 5.28 (s, 2H), 3.95 (s, 2H), 3.47 (d, J=3 Hz, 2H), 2.12 (m, 4H), 1.69 (m, 1H), 1.48 (m, 4H); MS (DCI/NH$_3$) m/e: 456 (M+H)$^+$. Anal. (C$_{29}$H$_{29}$O$_4$N) C, H, N.

Cell Growth Inhibition Assay. The sulforhodamine B assay was used according to the procedures developed and validated at NCI. The in vitro anticancer activities are expressed as ED$_{50}$ values, which is the test compound concentration (μM) that reduced the cell number by 50% after 72-h of continuous treatment. The values were interpolated from dose-response data. Each test was performed in triplicate with variation less than 5%. The ED$_{50}$ values determined in each of independent tests varied less than 10%. Compound stock solutions were prepared in DMSO with the final solvent concentration ≦1% DMSO (v/v), a concentration without effect on cell replication. The cells were cultured at 37° C. in RPMI-1640 supplemented with 25 mM N-2-hydroxyethylpipera-zine-N'-2-ethanesulfonic acid (HEPES), 2% (w/v) sodium bicarbonate, 10% (v/v) fetal bovine serum, and 100 μg/mL kanamycin in a humidified atmosphere containing 5% CO$_2$.

The foregoing is illustrative of the present invention, and is not to be construed as limiting thereof. The Invention is defined by the following claims, with equivalents of the claims to be included therein.

What is claimed is:

1. A compound of Formula I:

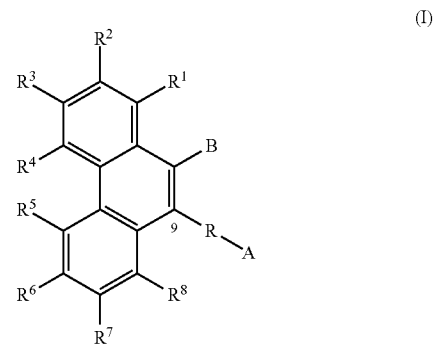

wherein:

R is C1-C4 alkylene;

B is H, halo, loweralkyl, or loweralkenyl; and

R$^1$, R$^2$, R$^3$, R$^4$, R$^5$, R$^6$, R$^7$ and R$^8$ are each independently selected from the group consisting of H, halo, alkoxy, loweralkyl, and loweralkenyl;

subject to the proviso that at least one of R$^2$, R$^3$, R$^4$, R$^5$, R$^6$ and R$^7$ is alkoxy;

and subject to the proviso that either (a) R$^2$ and R$^3$ together form —O—CH(R$^{10}$)—O—, or (b) R$^5$ and R$^6$ together form —O—CH(R$^{10}$)—O—, wherein R$^{10}$ is H, halo, or loweralkyl;

wherein A is —NR$^{11}$R$^{12}$, wherein R$^{11}$ is selected from the group consisting of H, alkyl, hydroxy, hydroxyalkyl, alkoxy, alkoxyalkyl, amino, and aminoalkyl, and wherein R$^{12}$ is selected from the group consisting of alkyl, hydroxy, hydroxyalkyl, alkoxy, alkoxyalkyl, amino, aminoalkyl, alkylaminoalkyl, alkylthio, and alkylthioalkyl;

or A is

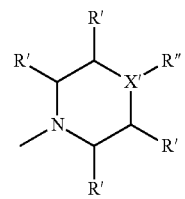

wherein:

X' is N or C, and each R' and R" is independently selected from the group consisting of H, alkyl, hydroxyalkyl, alkenyl, alkoxy, halo, oxo, =S, amino, alkoxyalkyl, alkylthiolkyl, and aryl;

and pharmaceutically acceptable salts thereof.

2. A compound of claim 1 having Formula Ia:

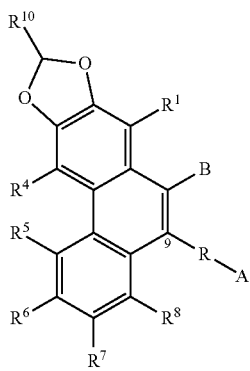
(Ia)

wherein A, B, R, R$^1$, R$^2$, R$^3$, R$^4$, R$^5$, R$^6$, R$^7$ R$^8$ and R$^{10}$ are as given above; and salts thereof.

3. A compound of claim 1 having Formula Ib:

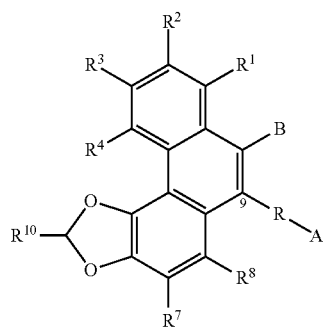
(Ib)

wherein A, B, R, R$^1$, R$^2$, R$^3$, R$^4$, R$^5$, R$^6$, R$^7$ R$^8$ and R$^{10}$ are as given above; and salts thereof.

4. A compound of Formula

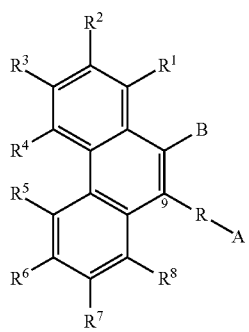
(I)

wherein:
R is C1-C4 alkylene;
A is selected from the group consisting of:

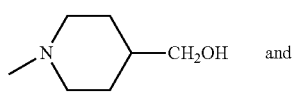 and

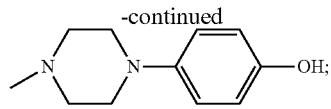

B is H, halo, loweralkyl, or loweralkenyl; and
R$^1$, R$^2$, R$^3$, R$^4$, R$^5$, $^6$, R$^7$ and R$^8$ are each independently selected from the group consisting of H, halo, alkoxy, loweralkyl, and loweralkenyl;
subject to the proviso that at least one of R$^2$, R$^3$, R$^4$, R$^5$, R$^6$ and R$^7$ is alkoxy;
and subject to the proviso that either (a) R$^2$ and R$^3$ together form) —O—CH(R$^{10}$)—O—, or (b) R$^5$ and R$^6$ together form —O—CH(R$^{10}$)—O—, wherein R$^{10}$ is H, halo, or loweralkyl;
and pharmaceutically acceptable salts thereof.

5. The compound of claim 4, wherein said compound is N-(2,3-Methylenedioxy-6-methoxy-phenanthr-9-ylmethyl)-(4-hydroxyphenyl)-piperazine (compound 29) or a pharmaceutically acceptable salt thereof.

6. The compound of claim 4, wherein said compound is N-(2,3-Methylenedioxy-6-methoxy-phenanthr-9-ylmethyl)-L-4-piperidinemethanol (compound 24a) or a pharmaceutically acceptable salt thereof.

7. A compound of Formula I:

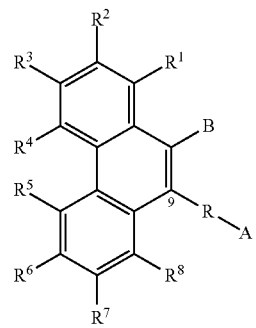
(I)

wherein:
R is C1-C4 alkylene;
A is —NR$^{11}$ R$^{12}$, wherein R$^{11}$ is selected from the group consisting of H, alkyl, hydroxy, hydroxyalkyl, alkoxy, alkoxyalkyl, amino, and aminoalkyl, and wherein R$^{12}$ is selected from the group consisting of alkyl, hydroxy, hydroxyalkyl, alkoxy, alkoxyalkyl, amino, aminoalkyl, alkylaminoalkyl, alkylthio, and alkylthioalkyl
B is H, halo, loweralkyl, or loweralkenyl; and
R$^1$, R$^2$, R$^3$, R$^4$, R$^5$, R$^6$, R$^7$ and R$^8$ are each independently selected from the group consisting of H, halo, alkoxy, loweralkyl, and loweralkenyl;
subject to the proviso that at least one of R$^2$, R$^3$, R$^4$, R$^5$, R$^6$ and R$^7$ is alkoxy;
and subject to the proviso that either (a) R$^2$ and R$^3$ together form —O—CH(R$^{10}$)—O—, or (b) R$^5$ and R$^6$ together form —O—CH(R$^{10}$)—O—, wherein R$^{10}$ is H, halo, or loweralkyl;
or a pharmaceutically acceptable salt thereof.

8. A pharmaceutical formulation comprising a compound of claim 1 in a pharmaceutically acceptable carrier.

9. The pharmaceutical formulation of claim 8, wherein said carrier is an aqueous carrier.

* * * * *

UNITED STATES PATENT AND TRADEMARK OFFICE
CERTIFICATE OF CORRECTION

PATENT NO. : 8,188,089 B2
APPLICATION NO. : 12/096950
DATED : May 29, 2012
INVENTOR(S) : Lee et al.

Page 1 of 4

It is certified that error appears in the above-identified patent and that said Letters Patent is hereby corrected as shown below:

In the Specifications:
Column 8, Line 5, Please correct the compound below:

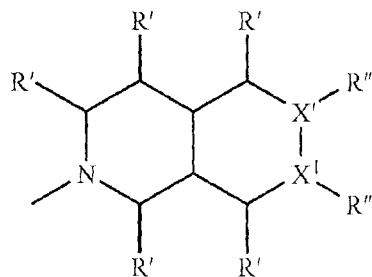

To read:

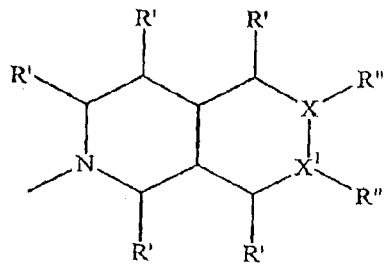

Columns 27-32, Scheme 2, Scheme 3, Table 4: Please move Scheme 2 and 3, and Table 4, along with corresponding paragraphs, to appear in the following order in the patent:

Signed and Sealed this
Twenty-eighth Day of May, 2013

Teresa Stanek Rea
*Acting Director of the United States Patent and Trademark Office*

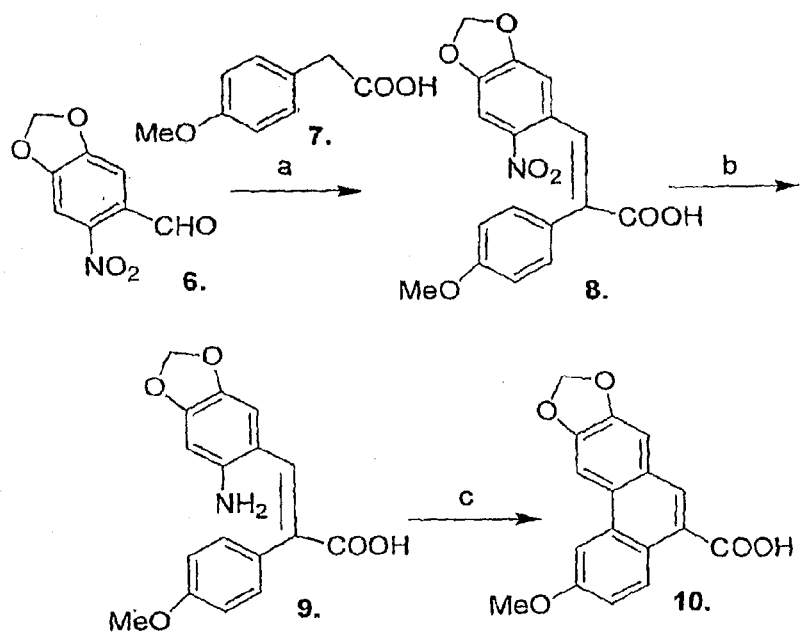

Reagents and conditions: a: $Ac_2O/Et_3N$  b: $FeSO_4/NH_4OH$
c: $NaNO_2$/Fluoroboric acid; Ferrocene/acetone.

Scheme 2

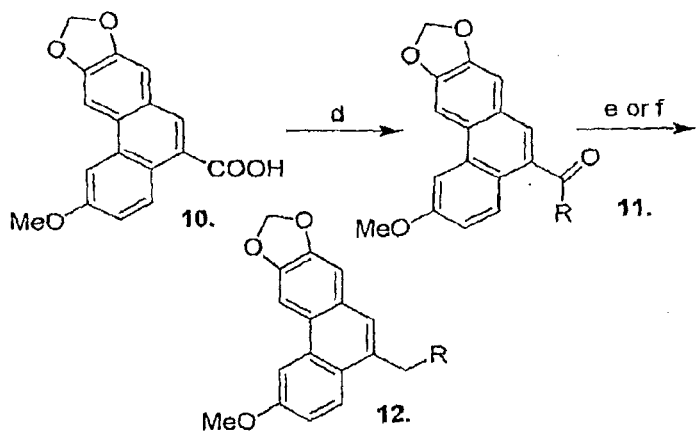

Reagents and conditions: d: EDC, DMAP, HOBt/DMF  e: BMS/THF  f: $LiAlH_4$/THF

Scheme 3

Results and Discussion. The in vitro anticancer activity of target compounds (13-32b) was evaluated first against the human A549 lung cancer cell line using the cell-based sulforhodamine B (SRB) microtitre plate assay (Rubinstein, L. V.; Shoemaker, R. H.; Paull, K. D.; Simon, R. M.; Tosini, S.; Skehan, P.; Scudiero, D. A.; Monks, M. R. Comparison of in vitro anticancer-drug-screening data generated with a tetrazolium assay versus a protein assay against a diverse panel of Human tumor cell lines. *J. Natl. Cancer Inst.* 1990, *82*, 1113-1118.). Compound structures and cytotoxic activity data against are shown in Table 4.

Table 4. *In vitro* anticancer activity against A549 lung cancer cells.

| Compound | R | A549 (μM) |
|---|---|---|
| 13 | -NH(CH$_2$)$_4$COOH | 1.3 |
| 14 | -NH(CH$_2$)$_4$CH$_2$OH | 0.27 |
| 15 | (S)-N-pyrrolidinyl-COOH | 2.1 |
| 16 | (S)-N-pyrrolidinyl-CH$_2$OH | 0.7 |
| 17 | (S)-N-piperidinyl-COOH | 0.5 |
| 18a | (S)-N-piperidinyl-CH$_2$OH | 0.16 |
| 19 | (R)-N-pyrrolidinyl-COOH | 5.2 |
| 20 | (R)-N-pyrrolidinyl-CH$_2$OH | 1.1 |

| | | |
|---|---|---|
| 21 | -NH(CH₂)₅COOH | 0.8 |
| 22a | -NH(CH₂)₅CH₂OH | 0.2 |
| 23 | -N(piperidine)-COOH | 0.23 |
| 24a | -N(piperidine)-CH₂OH | 0.08 |
| 25 | -NH(CH₂)₁₀COOH | 3.2 |
| 26 | -NH(CH₂)₁₀CH₂OH | 2.6 |
| 27 | -N(piperazine)-N-(2-Cl-phenyl) | NA |
| 28 | -N(piperazine)-N-(4-Cl-phenyl) | 65.2 |
| 29 | -N(piperazine)-N-(4-OH-phenyl) | 0.22 |
| 30 | -N(piperazine)-N-CH₂CH₂OH | 0.63 |
| 31 | -N(piperazine)-N-CH₂CH₂OCH₂CH₂OH | 57.1 |
| 32a | -N(piperidine)-CH₂CH₂OH | 0.15 |
| Emetine | | 0.04 |
| Doxorubicin | | 0.18 |
| Etoposide(VP-16) | | 1.4 |
| Antofine | | 0.008 |
| Vincristine | | 0.04 |

Twelve active compounds were further evaluated against three additional cancer cell lines (KB, DU145 and ZR-751) and one resistant subline (KB-Vin) (Table 5). Antofine, emetine, doxorubicin and etoposide (VP-16) were used as reference compounds.

In the Claims:
Column 41, Claim 4, Line 41: Please correct "of Formula" to read -- of Formula I: --